[19] United States Patent
Raddatz et al.

[11] Patent Number: 5,378,691
[45] Date of Patent: Jan. 3, 1995

[54] AMINO ACID DERIVATIVES

[75] Inventors: Peter Raddatz; Joachim Gante; Johannes Sombroek, all of Darmstadt; Claus J. Schmitges, Gross-Umstadt; Klaus-Otto Minck, Ober-Ramstadt, all of Germany

[73] Assignee: Merck Patent Gesellschaft Mit Beschrankter Haftung, Darmstadt, Germany

[21] Appl. No.: 213,365

[22] Filed: Aug. 15, 1994

Related U.S. Application Data

[63] Continuation-in-part of Ser. No. 739,147, Aug. 1, 1991, abandoned, which is a continuation-in-part of Ser. No. 337,785, Apr. 13, 1989, abandoned.

[30] Foreign Application Priority Data

Apr. 14, 1988 [DE] Germany .................. 3812328

[51] Int. Cl.$^6$ .................. A61K 37/02; C07K 5/08; C07K 5/10
[52] U.S. Cl. .................. 514/18; 514/17; 530/330; 530/331
[58] Field of Search .................. 514/18, 17; 530/330, 530/331

[56] References Cited

U.S. PATENT DOCUMENTS 4,845,079  7/1989  Luly et al. .................. 514/18
5,032,577  7/1991  Fung et al. .................. 514/18

FOREIGN PATENT DOCUMENTS 0081783  6/1983  European Pat. Off. ............ 530/331
0230242  7/1987  European Pat. Off. .

OTHER PUBLICATIONS

Burger, *Medicinal Chemistry*, 1960, pp. 565–571, 578, 581, 600–601.
Denkewalter et al. *Progress in Drug Research*, 1966, pp. 510–512.
Plattner et al., *J. Med. Chem.* 1988, 31(12): 2277–2288.
Bolis et al., *J. Med. Chem.* 1987, 30(10): 1729–1737.
Haber et al. *J. Cardiovasc. Res.*, 1987, 10 (suppl. 7) 554–558.
Wood et al., "Two–Kidney, One Clip Renal Hypertension in the Marmoset," *Journal of Hypertension*, vol. 4, No. 2, 1986, pp. 251–254.
Kempf et al., Proceedings of the Tenth American Peptide Symposium, May 23–28, St. Louis, Mo. (1987), pp. 474–475.

*Primary Examiner*—Lester L. Lee
*Attorney, Agent, or Firm*—Millen, White, Zelano, & Branigan

[57] ABSTRACT

New amino acid derivatives of the formula I $$R^1-C_pH_{2p}-(NH)_y-CO-NH-CH-R^2-CO-Z-C_mH_{2m}-CO-NH-CHR^3-CR^4-(CHR^5)_n-CO-E-Q-Y \quad I$$

in which $R^1$ to $R^5$, p, y, Z, m, n, E, Q and Y have the meanings defined herein, and the salts thereof, inhibit the activity of human plasma renin.

21 Claims, No Drawings

AMINO ACID DERIVATIVES

CROSS-REFERENCE TO RELATED APPLICATION

This application is a continuation of application Ser. No. 076/739,147, filed Aug. 1, 1991 now abandoned, which is a continuation-in-part of Ser. No. 07/337,785, filed Apr. 13, 1989 now abandoned.

SUMMARY OF THE INVENTION

The invention relates to new amino acid derivatives of the formula I

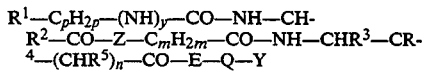

in which $R^1$ is $R^6R^7N-$, $R^6-NH-C(=NH)-NH-$, $NC-NH-C(=NH)-NH-$, $R^6OOC-$, $R^6O_3S-$ or $R^6-O-(CH_2CH_2O)_r-$, Z is $-O-$, $-CH_2-$, $-CH=CH-$, $-C\equiv C-$, $-NR^8-$, $-CH_2-O-$, $-CH_2-NR^8-$ or $-CH_2-S-$, E is 0 to 2 amino acid residues which are linked together in the manner of a peptide and are selected from the group comprising Abu, Ala, Cal, Gly, His, Ile, Leu, Met, Nle, Nva, Phe, Trp, Tyr and Val, Q is 0 or $NR^{10}$, Y is $-C_tH_{2t}-R^{11}$, $-C_tH_{2t}-R^{12}$ or $-C_wH_{2w}-(CR^{13})_s-C_tH_{2t}-R^{11}$, $R^2$, $R^3$ and $R^{11}$ are each H, A, Ar, Ar-alkyl, Het, Het-alkyl, cycloalkyl having 3-7 C atoms, cycloalkylalkyl having 4-11 C atoms, bicycloalkyl or tricycloalkyl each having 7-14 C atoms, bicycloalkylalkyl or tricycloalkylalky each having 8-18 C atoms, in each case being unsubstituted or singly or multiply substituted by A, AO and/or Hal.

$R^4$ and $R^{13}$ are each (H, OH), (H, $NH_2$) or $=O$, $R^5$, $R^8$ and $R^{10}$ are each H or A, $R^6$ and $R^7$ are each H, A or Ar-alkyl, $R^7$ is also $R^9-O-C_xH_{2x}-CO-$, $R^9-C_xH_{2x}-O-CO-$ or Ac, $R^9$ is A or Ar-alkyl, $R^6R^7N$ is also a piperidinyl, morpholinyl, piperazinyl or pyrrolidinyl group which is unsubstituted or substituted by A, OH, $NH_2$, NHA, $NA_2$, NHAc, $NH-CO-C_xH_{2x}-O-R^9$, $NH-CO-O-C_xH_{2x}-R^9$, $NH-SO_2-A$, hydroxyalkyl, COOH, COOA, $CONH_2$, CN, aminoalkyl, HAN-alkyl, $A_2$N-alkyl, $A_3N^\oplus$alkyl $An^\ominus$, $NH-CO-NH_2$, $NH-CO-NHA$, $NH-CO-NA_2$, guanidinyl or guanidinyl-alkyl, $R^{12}$ is $-SO_3H$, $-SO_2NH_2$, $-SO_2NHA$, $-SO_2NA_2$, $-NH_2$, $-NHA$, $-NA_2$, $-NH-C(=NH)-NH_2$, $-NH-C(=NH)-NHCN$, $-NH-CO-NH_2$, $-NH-CO-NHA$, $-NH-CO-NA_2$, $-NH-CS-NH_2$, $-NH-CS-NHA$, $-NH-CS-NA_2$, $-COOH$, $-COOA$, $-COO$-alkyl-Ar, $-CONH_2$, $-CONHA$ or $-CONA_2$, Y is 0 or 1, n and s are each 1 or 2, m, p, t, w and x are each 0, 1, 2, 3, 4, 5, 6, 7, 8, 9 or 10, r is 1, 2 or 3, Ar is phenyl which is unsubstituted or singly or multiply substituted by A, OA, Hal, $CF_3$, OH, $NO_2$, hydroxyalkyl, $NH_2$, NHA, $NA_2$, NHAc, SA, $SO-A$, $SO_2-A$, $SO_2NH_2$, $SO_2NHA$, COOH, COOA, $CONH_2$, CN, aminoalkyl, HAN-alkyl, $A_2$N-alkyl, $A_3N^\oplus$alkyl $An^\ominus$ and/or guanidinyl-alkyl, or is unsubstituted naphthyl, Het is a saturated or unsaturated 5- or 6-membered heterocyclic radical which has 1-4 N, O and/or S atoms and can be fused with a benzene ring and/or can be singly or multiply substituted by A, OA, Hal, $CF_3$, OH, $NO_2$, carbonyl oxygen, $NH_2$, NHA, $NA_2$, NHAc, SA, $SO-A$, $SO_2-A$, $SO_2NH_2$, $SO_2NHA$, COOH, COOA, $CONH_2$, CN, $NH-SO_2-A$, Ar, Ar-alkyl, Ar-alkenyl, hydroxyalkyl and/or aminoalkyl, and/or whose N and/or S hetero atoms can also be oxidized, Hal is F, Cl, Br or I, Ac is $H-CO-$, $A-CO-$, $CF_3-CO-$, $Ar-CO-$, Ar-alkyl-CO$-$ or $A-NH-CO-$, $An^\ominus$ is an anion, which can also be absent if, in its stead, a carboxyl group contained in the compound of the formula I is in the form of a carboxylate anion, -alkyl- is an alkylene group having 1-8 C atoms, and A is alkyl having 1-8 C atoms, in which, furthermore, it is also possible for one or more $-NH-CO-$ groups to be replaced by one or more $-NA-CO-$ groups, as well as the salts thereof.

In the foregoing, selection of variables defined together is made independently.

Similar compounds are disclosed in EP-A 249096. Indicated therein is a formula "I" which also embraces some of the compounds of the present formula I, especially some of those compounds of the formula I in which $R^1-C_pH_{2p}-(NH)_y-CO-$ is $R^6R^7N-C_pH_{2p}-CO-$, $R^6$ and $R^7$ are each H or alkyl, and p is 0, 1, 2, 3, 4 or 5. Neither the latter group of compounds nor any individual compound covered thereby is, however, mentioned in EP-A 249096, nor is it possible to deduce from anywhere in this publication that particularly this group of compounds has especially advantageous properties.

It is an object of the invention to provide new compounds with valuable properties, in particular those which can be used for the preparation of medicaments.

Upon further study of the specification and appended claims, further objects and advantages of this invention will become apparent to those skilled in the art.

It has been found that the compounds of the formula I and the salts thereof have very valuable properties. In particular, they inhibit the activity of human plasma renin. This action can be detected, for example, by the method of F. Fyhrquist et al., Clin. Chem. 22, 250-256 (1976). The noteworthy point is that these compounds are very specific inhibitors of renin; as a rule, the concentrations of these compounds necessary for the inhibition of other aspartyl proteinases (for example pepsin and cathepsin D) are about 100 to 1000 times as high as for renin inhibition. The actions of the compounds on the blood pressure and/or on the heart rate, as well as the inhibition of renin activity in blood plasma can furthermore be determined in conscious monkeys, for example female monkeys (*Macaca fascicularis*); it is possible in this for the blood pressure and heart rate to be measured by a modification of the method of M.J. Wood et al., J. Hypertension 4, 251-254 (1985). In order to stimulate renin activity in this, the animals are preferably pretreated with a saluretic. Blood samples for the determination of the plasma renin activity can be obtained by puncture of the femoral vein.

The compounds can be used as pharmaceutically active substances in human and veterinary medicine, in particular for the prophylaxis and for the treatment of diseases of the heart, circulation and vessels, especially of hypertension, cardiac insufficiency and hyperaldosteronism. In addition, the compounds can be used for diagnostic purposes in order to determine, in patients with hypertension or hyperaldosteronism, the possible contribution of the renin activity to maintaining the pathological state. The procedure for such diagnostic tests can be similar to that indicated in EP-A 77 028.

The abbreviations quoted hereinbefore and hereinafter for amino acid residues represent the radicals —NR'—R''—CO—, as a rule —NH—CHR—CO— (in which R, R' and R'' have the specific meaning known for each amino acid), of the following amino acids:

Abu 2-Aminobutyric acid
AHCH 4S-Amino-3S-hydroxy-6-cyclohexyl-hexanoic acid
AHCP 4S-Amino-3S-hydroxy-5-cyclohexyl-pentanoic acid
AHPP 4S-Amino-3S-hydroxy-5-phenyl-pentanoic acid
Ala Alanine
βAla β-Alanine
Cal 3-Cyclohexylalanine
DACH 3S,4S-Diamino6-cyclohexyl-hexanoic acid
DACP 3S,4S-Diamino-5-cyclohexyl-pentanoic acid
DAMH 3S,4S-Diamino-6-methyl-heptanoic acid
DAPP 3S,4S-Diamino-5-phenyl-pentanoic acid
Gly Glycine
His Histidine
Ile Isoleucine
Leu Leucine
Mal 3-(p-Methoxyphenyl)-alanine
Met Methionine
αNal 3-(α-Naphthyl)-alanine
βNal 3-(β-Naphthyl)-alanine
Nle Norleucine
N-Me-His N-Methyl-histidine
N-Me-Phe N-Methyl-phenylalanine
Nva Norvaline
p-F-Phe Phenylalanine substituted by F in the para position.
Phe Phenylalanine
Pia 3-(Piperidyl)-alanine [e.g. 2-Pia=3-(2-piperidyl)-alanine]
Pya 3-(Pyridyl)-alanine [e.g. 3-Pya=3-(3-pyridyl)-alanine]
Sta Statine
Tia 3-(Thienyl)-alanine [e.g. 2-Tia=3-(2-thienyl)-alanine]
Trp Tryptophan
Tyr Tyrosine
Val Valine.

Further meanings hereinafter are:
ADPA N-2-Amino-5,6-dimethyl-3-pyrazinylmethylamide
AMPA N-4-Amino-2-methyl-5-pyrimidinylmethylamide
BOC tert.-Butoxycarbonyl
BOM Benzyloxymethyl
imi-BOM Benzyloxymethyl in the 1 position of the imidazole ring
CBZ Benzyloxycarbonyl
DCCI Dicyclohexylcarbodiimide
DMF Dimethylformamide
DNP 2,4-Dinitrophenyl
imi-DNP 2,4-Dinitrophenyl in the 1 position of the imidazole ring
ETOC Ethoxycarbonyl
FMOC 9-Fluorenylmethoxycarbonyl
HOBt 1-Hydroxybenzotriazole
IPOC Isopropoxycarbonyl
OMe Methyl ester
OEt Ethyl ester
POA Phenoxyacetyl
THF Tetrahydrofuran.

If the abovementioned amino acids can occur in more than one enantiomeric form, then all these forms, as well as mixtures thereof (for example the DL forms), are included hereinbefore and hereinafter, for example as constituents of the compounds of the formula I. The L forms are preferred. Where individual compounds are mentioned hereinafter, then the abbreviations of these amino acids each relate to the L form unless expressly indicated otherwise.

The invention furthermore relates to a process for the preparation of an amino acid derivative of the formula I, and of the salts thereof, characterized in that it is liberated from one of its functional derivatives by treatment with a solvolyzing or hydrogenolyzing agent, or in that a carboxylic acid of the formula II

  II in which $G^1$ is
(a) absent,
(b) —NH—CHR$^2$—CO—,
(c) —NH—CHR$^2$—CO—Z—C$_m$H$_{2m}$—CO—,
(d) —NH—CHR$^2$—CO—Z—C$_m$H$_{2m}$—CO—W—,
(e) —NH—CHR$^2$—CO—Z—C$_m$H$_{2m}$—CO—W—E$^1$—,
(f) —NH—CHR$^2$—CO—Z—C$_m$H$_{2m}$—CO—W—E— and
W is —NH—CHR$^3$—CR$^4$—(CHR$^5$)$_n$—CO— or one of the reactive derivatives thereof, is reacted with an amino compound of the formula III

  III in which $G^2$ is
(a) —NH—CHR$^2$—CO—Z—C$_m$H$_{2m}$—CO—W—E—Q—Y,
(b) —Z—C$_m$H$_{2m}$—CO—W—E—Q—Y,
(c) —W—E—Q—Y,
(d) —E—Q—Y,
(e) —E$^2$—Q—Y,
(f) —NR$^{10}$—Y and $E^1+E^2$ are together E, and in that a functionally modified amino and/or hydroxyl group in a compound of the formula I is liberated where appropriate by treatment with solvolyzing or hydrogenolyzing agents, and/or for the preparation of a compound of the formula I, $R^4$=(H, OH) or (H, NH$_2$), an amino keto acid derivative of the formula I, $R^4$=O, is reduced or reductively aminated, and/or one radical $R^1$ is converted to another radical $R^1$ and/or a compound of the formula I is converted by treatment with an acid into one of the salts thereof.

Hereinbefore and hereinafter the radicals and parameters $R^1$ to $R^{13}$, Z, E, Q, Y, m, n, p, r, s, t, w, x, y, Ar, Het, Hal, Ac, An$\ominus$, A, $G^1$, $G^2$, $E^1$, $E^2$ and W have the meanings indicated for the formulae I, II or III unless expressly indicated otherwise.

A in the formulae mentioned hereinbefore has 1-8, preferably 1, 2, 3 or 4, C atoms. A is preferably methyl, furthermore ethyl, propyl, isopropyl, butyl, isobutyl, sec.-butyl or tert.-butyl, as well as pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl.

Typically, all "alkyl" and "alkenyl" portions mentioned above have up to 8 C atoms, including, for example, the alkylene and alkenyl portions of Ar-alkenyl, Ar-alkyl, guanidinyl-alkyl, HAN-alkyl, Ar-alkyl-CO and $A_3N^\oplus$ alkyl $An^\ominus$.

Cycloalkyl is preferably cyclopropyl, cyclobutyl, cyclopentyl, cyclohexyl or cycloheptyl, but is also, for example, 1-, 2- or 3-methylcyclopentyl, or 1-, 2-, 3- or 4-methylcyclohexyl.

Correspondingly, cycloalkylalkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl, but is also, for example, 1-, 2- or 3-methylcyclopentylmethyl, or 1-, 2-, 3- or 4-methylcyclohexylmethyl.

Bicycloalkyl is preferably 1- or 2-decalyl, 2-bicyclo[2.2.1]heptyl or 6,6-dimethyl-2-bicyclo[3.1.1]heptyl.

Tricycloalkyl is preferably 1-adamantyl.

Hal is preferably F, Cl or Br, but is also i.

Ac is preferably A—CO—, such as acetyl, propionyl or butyryl, Ar—CO— such as benzoyl, o-, m- or p-methoxybenzoyl or 3,4-dimethoxybenzoyl, or A—N-H—CO— such as N-methyl-or N-ethylcarbamoyl.

Ar is preferably phenyl and is furthermore preferably o-, m- or p-tolyl, o-, m- or p-ethylphenyl, o-, m- or p-methoxyphenyl, o-, m- or p-fluorophenyl, o-, m-or p-chlorophenyl, o-, m- or p-bromophenyl, o-, m- or p-iodophenyl, o-, m- or p-trifluoromethylphenyl, o-, m-or p-hydroxyphenyl, o-, m- or p-sulfamoylphenyl, 2,3-, 2,4-, 2,5-, 2,6-, 3,4- or 3,5-dimethoxyphenyl, 3,4,5-trimethoxyphenyl, o-, m- or p-aminophenyl, o-, m- or p-aminomethylphenyl, o-, m- or p-dimethylaminomethylphenyl, o-, m- or p-guanidinomethylpheny, or 1- or 2-naphthyl.

Correspondingly, Ar-alkyl is preferably benzyl, 1-or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxybenzyl, 1-or 2-o-, -m- or -p-methoxy-phenylethyl, o-, m- or p-fluorobenzyl, 1- or 2-o-, -m- or -p-fluorophenylethyl, o-, m- or p-chlorobenzyl, 1- or 2-o-, -m- or -p-chlorophenylethyl, o-, m- or p-bromobenzyl, 1- or 2-o-, -m- or -p-bromophenylethyl, o-, m- or p-iodobenzyl, 1- or 2-o-, -m- or -p-iodophenylethyl, o-, m- or p-trifluoromethylbenzyl, o-, m- or p-hydroxybenzyl, 2,3-, 2,4-, 2,5-, 2,6-, 3,4- or 3,5-dimethoxybenzyl, 3,4,5-trimethoxybenzyl, o-, m- or p-aminobenzyl, o-, m- or p-aminomethylbenzyl, o-, m- or p-dimethylaminomethylbenzyl, o-, m- or p-guanidinomethylbenzyl, or 1- or 2-naphthylmethyl.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4-or -5-yl, 1,2,4-oxadiazol-3- or -5-yl, 1,3,4-thiadiazol-2-or -5-yl, 1,2,4-thiadiazol-3- or -5-yl, 2,1,5-thiadiazol-3- or -4-yl, 2-, 3-, 4-, 5- or 6-2H-thiopyranyl, 2-, 3- or 4-4H-thiopyranyl, 3- or 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6-or 7-indolyl, 1-, 2-, 3-, 4-, 5-, 6-or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolyl, 2-, 4-, 5-, 6-, 7- or 8-quinazolyl. The heterocyclic radicals can also be partially or completely hydrogenated. Thus, Het can also be, for example, 2,3-dihydro-2-, -3-, -4- or -5-furyl, 2,5-dihydro-2-, -3-, -4- or -5-furyl, tetrahydro-2-or -3-furyl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4-or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The heterocyclic radicals can also be substituted as indicated. Het can also preferably be, for example, 2-amino-4-thiazolyl, 4-carboxy-2-thiazolyl, 4-caroampyl-2-thiazolyl, 4-(2-aminoethyl)-2-thiazolyl, 4-amino-2-methyl-5-pyrimidinyl, 2-amino-5,6-dimethyl-3-pyrazinyl, 4-carbamoyl-piperidino, furthermore, for example, 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3-methyl-5-tert.-butyl-2-thienyl, 5-chloro-2-thienyl, 3-phenyl-2- or -3-thienyl, 1-, 3-, 4- or 5-methyl-2-pyrrolyl, 1-methyl-4- or -5-nitro-2-pyrrolyl, 3,5-dimethyl-4-ethyl-2-pyrrolyl, 4-methyl-5-pyrazolyl, 5-methyl-3-isoxazolyl, 3,4-dimethyl-5-isoxazolyl, 4- or 5-methyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl-2-pyridyl, 2-, 4-, 5- or 6-methyl-3-pyridyl, 2- or 3-methyl-4-pyridyl, 3-, 4-, 5- or 6-chloro-2-pyridyl, 2-, 4-, 5- or 6-chloro-3-pyridyl, 2- or 3-chloro-4-pyridyl, 2,6-dichloropyridyl, 2-hydroxy-3-, -4-, -5- or -6-pyridyl (=1H-2-pyridon-3-, -4-, -5- or 6-yl), 5-phenyl-1H-2-pyridon-3-yl, 5-p-methoxyphenyl-1H-2-pyridon-3-yl, 2-methyl-3-hydroxy-4-hydroxymethyl-5-pyridyl, 2-hydroxy-4-amino-6-methyl-3-pyridyl, 3-N'-methylureido-1H-4-pyridon-5-yl, 4-methyl-2-pyrimidinyl, 4,6-dimethyl-2-pyrimidinyl, 2-, 5- or 6-methyl-4-pyrimidinyl, 2,6-dimethyl-4-pyrimidinyl, 2,6-dihydroxy-4-pyrimidinyl, 5-chloro-2-methyl-4-pyrimidinyl, 3-methyl-2-benzofuryl, 2-ethyl-3-benzofuryl, 7-methyl-2-benzothienyl, 1-, 2-, 4-, 5-, 6- or 7-methyl-3-indolyl, 1-methyl-5- or -6-benzimidazolyl, 1-ethyl-5- or -6-benzimidazolyl, 3-, 4-, 5-, 6-, 7- or 8-hydroxy-2-quinolyl, 2-oxo-pyrrolidino, 2-oxo-piperidino, 2,5-dioxopyrrolidino or 3-benzyl-2,5-dioxopyrrolidino.

$R^1$ is preferably $R^6R^7N$ or $R^6OOC$.

Z is preferably —NR$^8$—, in particular —NH— or —N(CH$_3$)—, furthermore preferably —CH$_2$—, —CH$_2$—O—, —CH$_2$—NR$^8$— (in particular —CH$_2$—NH—) or —CH$_2$—S—. Correspondingly, —Z—C$_m$H$_{2m}$—CO— is preferably Gly or βAla, furthermore preferably —CH$_2$CH$_2$—CO—, —CH$_2$CH$_2$CH$_2$—CO— or —CH$_2$—S—CH$_2$—CO—.

The parameter y is preferably 0; n and s are preferably each 1; m is preferably 1 or 2, furthermore preferably 0; p is preferably 1, 2, 3, 4 or 5, furthermore 6 or 7; r is preferably 1 or 2. The groups C$_m$H$_{2m}$ and C$_p$H$_{2p}$ are preferably —(CH$_2$)$_m$—, in particular —CH$_2$—, or —(CH$_2$)$_p$—, in particular —CH$_2$—, —(CH$_2$)$_2$—, —(CH$_2$)$_4$— or —(CH$_2$)$_5$—. The groups C$_t$H$_{2t}$ and C$_w$H$_{2w}$ are preferably each —CH$_2$—, —(CH$_2$)$_2$—, —CH(CH$_3$)—, —CH(isobutyl)— or —CH(sec.-butyl)—; it is also possible and preferable for the group C$_t$H$_{2t}$ to be absent (t=0). The parameter x is preferably 1, furthermore 0 or 2.

R$^2$ is preferably Ar-alkyl, in particular benzyl, 1- or 2-naphthylmethyl, furthermore preferably cycloalkylalkyl, in particular cyclohexylmethyl, as well as Het-alkyl, in particular 2-, 3- or 4-piperidylmethyl, 2-, 3- or 4-pyridylmethyl, 2- or 3-thienylmethyl. Accordingly, the group —NH—CHR$^2$—CO— is preferably Phe, and is furthermore preferably Mal, αNal, βNal, Cal, Pia, Pya or Tia.

R$^3$ is preferably cyclohexylmethyl, furthermore preferably A, in particular methyl, ethyl, propyl, isopropyl, butyl, isobutyl, sec.-butyl, pentyl, isopentyl (3-methylbutyl) or 2-methylbutyl, phenyl, benzyl, p-chlorobenzyl, 2-cyclohexylethyl, bicyclo[2.2.1]heptyl-2-methyl or 6,6-dimethylbicyclo[3.1.1]heptyl-2-methyl.

R$^4$ and R$^{13}$ are each preferably (H, OH).

R$^5$, R$^6$, R$^7$, R$^8$ and R$^{10}$ are each preferably H or methyl, furthermore ethyl, propyl, isopropyl, butyl or isobutyl, and R$^7$ is also preferably benzyl, alkoxycarbonyl such as ETOC, IPOC or BOC or Ar-alkoxycarbonyl such as CBZ, and R$^6$R$^7$N is also preferably pyrrolidino, piperidino or 4-methylpiperidino.

Accordingly, the group R$^1$—C$_p$H$_{2p}$—(NH)$_y$—CO— is preferably R$^1$—C$_p$H$_{2p}$—CO—, in particular R$^1$—(CH$_2$)$_p$—CO—, specifically and in particular R$^6$R$^7$N—C$_p$H$_{2p}$—CO—, preferably R$^6$R$^7$N—(CH$_2$)$_p$—CO—, especially H$_2$N—C$_p$H$_{2p}$—CO—, such as aminocarbonyl, aminoacetyl (H-Gly-), 3-aminopropionyl (H-βAla-), 4-amino-butyryl, 5-aminopentanoyl, 6-aminohexanoyl, 7-aminoheptanoyl, 8-aminooctanoyl, 9-aminononanoyl, 10-aminodecanoyl, 11-aminoundecanoyl, but also, for example, 2-amino-propionyl (Ala), 2-amino-2-methylpropionyl; ANH—C$_p$H$_{2p}$—CO— such as methylaminocarbonyl, methylaminoacetyl (sarcosyl), 3-methylaminopropionyl, 4-methylaminobutyryl, 5-methylaminopentanoyl, 6-methylaminohexanoyl, 6-ethylaminohexanoyl, 7-methylaminoheptanoyl, 8-methylaminooctanoyl, 9-methylaminononanoyl, 10-methylaminodecanoyl, 11-methylaminoundecanoyl; A$_2$N—C$_p$H$_{2p}$—CO— such as dimethylaminocarbonyl, dimethylaminoacetyl, 3-dimethylaminopropionyl, 4-dimethylaminobutyryl, 5-dimethylaminopentanoyl, 6-dimethylaminohexanoyl, 6-diethylaminohexanoyl, 7-dimethylaminoheptanoyl, 8-dimethylaminooctanoyl, 9-dimethylaminononanoyl, 10-dimethylaminodecanoyl, 11-dimethylaminoundecanoyl; A—O—CO—N-H—C$_p$H$_{2p}$—CO— such as BOC-Gly, ETOC-Gly-, IPOC-Gly, BOC-βAla, ETOC-βAla, IPOC-βAla-, 4-BOC-amino-butyryl, 5-BOC-amino-pentanoyl, 6-BOC-amino-hexanoyl, 7-BOC-amino-heptanoyl, 8-BOC-amino-octanoyl, 9-BOC-amino-nonanoyl, 10-BOC-amino-decanoyl, 11-BOC-amino-undecanoyl; ArCH$_2$—O—CO—NH—C$_p$H$_{2p}$—CO— such as CBZ-Gly-, CBZ-βAla, 4-CBZ-amino-butyryl, 5-CBZ-amino-hexanoyl, 7-CBZ-amino-heptanoyl, 8-CBZ-amino-octanoyl, 9-CBZ-amino-nonanoyl, 10-CBZ-amino-decanoyl, 11-CBZ-amino-undecanoyl; Pyrrolidino-C$_p$H$_{2p}$—CO— such as pyrrolidinocarbonyl, pyrrolidino-acetyl, 3-pyrrolidino-propionyl, 4-pyrrolidino-butyryl, 5-pyrrolidino-pentanoyl, 6-pyrrolidino-hexanoyl, 4-pyrrolidino-heptanoyl, 8-pyrrolidino-octanoyl, 9-pyrrolidino-nonanoyl, 10-pyrrolidino-decanoyl; piperidino-C$_p$H$_{2p}$—CO— such as piperidinocarbonyl, piperidinoacetyl, 3-piperidino-propionyl, 4-piperidino-butyryl, 5-piperidino-pentanoyl, 6-piperidino-hexanoyl, 7-piperidinoheptanoyl, 8-piperidino-octanoyl, 9-piperidino-nonanoyl, 10-piperidino-decanoyl; morpholino-C$_p$H$_{2p}$—CO— such as morpholinocarbonyl, morpholinoacetyl, 3-morpholino-propionyl, 4-morpholino-butyryl, 5-morpholino-pentanoyl, 6-morpholino-hexanoyl, 7-morpholino-heptanoyl, 8-morpholino-octanoyl, 9-morpholino-nonanoyl, 10-morpholino-decanoyl; 4-amino-piperidino-C$_p$H$_{2p}$—CO— such as 4-amino-piperidino-carbonyl, 4-amino-piperidino-acetyl, 3-(4-amino-piperidino)-propionyl, 4-(4-amino-piperidino)-butyryl, 5-(4-amino-piperidino-pentanoyl, 6-(4-amino-piperidino)-hexanoyl, 7-(4-amino-piperidino)-heptanoyl, 8-(4-amino-piperidino)-octanoyl, 9-(4-amino-piperidino)-nonanoyl, 10-(4-amino-piperidino)-decanoyl; 4-dialkylamino-piperidino-C$_p$H$_{2p}$—CO— such as 4-dimethylamino-piperidinocarbonyl, 4-dimethylaminopiperidino-acetyl; 4-guanidino-piperidino-C$_p$H$_{2p}$—CO— such as 4-guanidino-piperidino-carbonyl, 4-guanidino-piperidino-acetyl; 4-carboxy-piperidino-C$_p$H$_{2p}$—CO— such as 4-carboxy-piperidino-carbonyl, 4-carboxy-piperidino-acetyl; 4-alkoxycarbonyl-piperidino-C$_p$H$_{2p}$—CO— such as 4-methoxycarbonyl-piperidino-carbonyl, 4-ethoxycarbonyl-piperidino-carbonyl, 4-methoxycarbonyl-piperidino-acetyl, 4-ethoxycarbonylpiperidino-acetyl; 4-AcNH-piperidino-C$_p$H$_{2p}$—CO— such as 4-acetamido-piperidino-carbonyl, 4-acetamidopiperidino-acetyl; H$_2$N—C(=NH)—NH—C$_p$H$_{2p}$—CO— such as guanidinoacetyl, 3-guanidinopropionyl, 4-guanidino-butyryl, 5-guanidino-pentanoyl, 6-guanidino-hexanoyl, 7-guanidinoheptanoyl, 8-guanidino-octanoyl; NC—NH—C(=NH)—NH—C$_p$H$_{2p}$—CO— such as N'-cyanoguanidino-acetyl, 3-(N'-cyanoguanidino)-propionyl, 4-(N'-cyanoguanidino)-butyryl; 5-(N'-cyanoguanidino)-pentanoyl, 6-(N'-cyanoguanidino)-hexanoyl, 7-(N'-cyanoguanidino)-heptanoyl, 8-(N'-cyanoguanidino)-octanoyl; HOOC—C$_p$H$_{2p}$—CO— such as malonyl, succinyl, glutaryl, adipyl, 6-carboxyhexanoyl, 7-carboxyheptanoyl, 8-carboxyoctanoyl, 9-carboxynonanoyl, 10-carboxy-decanoyl, 11-carboxyundecanoyl; AOOC—C$_p$H$_{2p}$—CO— such as methoxycarbonyl-acetyl, 3-methoxycarbonyl-propionyl, 4-methoxycarbonyl-butyryl, 5-methoxycarbonyl-pentanoyl, 6-methoxycarbonyl-hexanoyl, 7-methoxycarbonyl-heptanoyl, 8-methoxycarbonyl-octanoyl, 9-methoxycarbonyl-nonanoyl, 10-methoxycarbonyl-decanoyl, ethoxycarbonyl-acetyl, 3-ethoxycarbonyl-propionyl, 4-ethoxycarbonyl-butyryl, 5-ethoxycarbonyl-pentanoyl, 6-ethoxycarbonyl-hexanoyl, 7-ethoxycarbonyl-heptanoyl, 8-ethoxycarbonyl-octanoyl, 9-ethoxycarbonyl-nonanoyl, 10-ethoxycarbonyl-decanoyl; H—SO$_3$—C$_p$H$_{2p}$—CO— such as sulfo-acetyl, 3-sulfo-propionyl, 4-sulfo-butyryl, 5-sulfo-pentanoyl, 6-sulfo-hexanoyl, 7-sulfo-heptanoyl, 8-sulfo-octanoyl, 9-sulfo-nonanoyl, 10-sulfo-decanoyl; A—SO$_3$—C$_p$H$_{2p}$—CO— such as methoxysulfonyl-acetyl, 3-methoxysulfonyl-propionyl, 4-methoxysulfonyl-butyryl, 5-methoxysulfonyl-pentanoyl, 6-methoxysulfonyl-hexanoyl, 7-methoxysulfonyl-heptanoyl, 8-methoxysulfonyl-octanoyl, 9-methoxysulfonyl-nonanoyl, 10-methoxysulfonyl-decanoyl, ethoxysulfonyl-acetyl, 3-ethoxysulfonyl-propionyl, 4-ethoxysulfonyl-butyryl, 5-ethoxysulfonyl-pentanoyl, 6-ethoxysulfonyl-hexanoyl, 7-ethoxysulfonyl-heptanoyl, 8-ethoxysulfonyl-octanoyl, 9-ethoxysulfonyl-nonanoyl, 10-ethoxysulfonyl-decanoyl; A—O—(CH$_2$CH$_2$O)$_r$—C$_p$H$_{2p}$—CO— such as 3,6-dioxa-heptanoyl, 3,6- or 4,7-dioxa-octanoyl, 3,6-, 4,7- or 5,8-dioxa-nonanoyl, 3,6,9-trioxa-decanoyl, 3,6,9- or 4,7,10-trioxa-undecanoyl, 3,6,9-; 4,7,10- or 5,8,11-trioxa-dodecanoyl.

If n is 2, the two radicals R$^5$ can be identical to or different from one another; in the latter case, preferably one radical R$^5$ is H and the other is A, in particular isopropyl, and the group —(CHR$^5$)$_n$— is preferably —CH$_2$—CHA—, in particular —CH$_2$—CH(isopropyl)-

R$^9$ is preferably methyl, ethyl, propyl, isopropyl, butyl, isobutyl, sec.-butyl, tert.-butyl or benzyl.

The group W is preferably —NH—CHR$^3$—CHOH—CH$_2$—CO—, in particular AHCP, AHCH, Sta or AHPP. The group W is furthermore preferably —NH—CHR$^3$—CH(NH$_2$)—CH$_2$—CO—, in particular DACP, DACH, DAMH or DAPP.

The group W has at least one chiral center. Further chiral centers may be present in the groups R$^1$ to R$^5$, C$_p$H$_{2p}$, C$_m$H$_{2m}$, Z, E, Q and Y. The compounds of the formula I can therefore occur in various, optically inactive or optically active, forms. The formula I embraces all these forms. If W is —NH—CHR$^3$—CR$^4$—CH$_2$—CO— with R$^4$ being (H, OH) or (H, NH$_2$), the 3S-hydroxy-4S-amino enantiomers and 3S,4S-diamino enantiomers are preferred. The abbreviations AHCP, AHCH, Sta, AHPP, DACP, DACH, DAMH and DAPP always relate to the 3S,4S forms.

E is preferably one of the said amino acid residues, in particular Ile or Leu; furthermore, E is preferably absent or is preferably Abu, Cal, Met, Nle, Nva, Phe or Val.

Q is preferably NR$^{10}$, in particular NH or N(CH$_3$).

Y is preferably —C$_t$H$_{2t}$—R$^{11}$ or —C$_t$H$_{2t}$—R$^{12}$, in particular —CH$_2$R$^{11}$, —CH$_2$R$^{12}$ or —CH$_2$CH$_2$R$^{12}$. In these, R$^{11}$ is preferably H, A, Ar or Het, specifically and preferably H, alkyl having 3–5 C atoms, phenyl, o-, m- or p-aminomethylphenyl, o-, m- or p-guanidinomethylphenyl, o-, m- or p-dialkylaminomethylphenyl, such as o-, m- or p-dimethylaminomethylphenyl, 2-, 3- or 4-pyridyl, 2-hydroxy-4,6-dimethyl-3-pyridyl, 4-amino-2-methyl-5-pyrimidinyl or 2-amino-5,6-dimethyl-3-pyrazinyl. R$^{12}$ is preferably —SO$_3$H, —SO$_2$NH$_2$, —NA$_2$, —NA$_3{}^+$An$^-$, —NH—C(=NH)—NH$_2$, —NH—CO—NHA or —NH—CS—NHA, wherein A is preferably CH$_3$.

Some particularly preferred meanings of the group Q—Y are —NH—CH$_2$—(4-amino-2-methyl-5-pyrimidinyl) ("AMPA"), —NH—CH$_2$—(2-amino-5,6-dimethyl-3-pyrazinyl) ("ADPA") and —NH—CH$_2$—(3-pyridyl), furthermore —NH—A.

The above-mentioned cyclic groups, especially the cycloalkyl and phenyl groups, are preferably unsubstituted or preferably have 1 to 3, in particular 1 or 2, substituents.

Accordingly, the invention particularly relates to those compounds of the formula I in which at least one of the said radicals has one of the preferred meanings indicated hereinbefore. Some preferred groups of compounds can be represented by the following part-formulae Ia to Ii, which correspond to the formula I but in which in Ia
  R$^1$ is R$^6$R$^7$N—;
in Ib
  R$^1$ is R$^6$—NH—C(=NH)—NH or NC—NH—C(=NH)—NH;
in Ic
  R$^1$ is R$^6$OOC—;
in Id
  R$^1$ is R$^6$O$_3$S—;
in Ie
  R$^1$ is R$^6$—O—(CH$_2$CH$_2$O)$_r$—;
in If
  R$^1$ is R$^6$R$^7$N—,
  R$^6$ is H or A,
  R$^7$ is H, A, BOC or CBZ,
  R$^6$R$^7$N is also 4-aminopiperidino,
  y is 0 and
  p is 0, 1, 2, 3, 4, 5, 6 or 7;
in Ig
  R$^1$ is R$^6$OOC—,
  R$^6$ is H or A and
  y is 0;
in Ih
  R$^1$ is R$^6$O$_3$S—,
  R$^6$ is H or A and
  y is 0;
in Ii
  R$^6$R$^7$N is 4-aminopiperidino and
  y and p are each 0.

Particularly preferred compounds are those of the part-formulae:

(a) Iaa to Iia, which correspond to the formulae Ia to Ii but in which additionally R$^2$ is phenyl or p-methoxyphenyl;

(b) Iab to Iib as well as Iaab to Iiab, which correspond to the formulae Ia to Ii and Iaa to Iia but in which additionally —Z—C$_m$H$_{2m}$— is —NH—CH$_2$— or —NH—CH$_2$CH$_2$—;

(c) Iac to Iic, Iaac to Iiac, Iabc to Iibc and Iaabc to Iiabc, which correspond to the formulae Ia to Ii, Iaa to Iia, Iab to Iib and Iaab to Iiab but in which additionally —NH—CHR$^3$—CR$^4$—(CHR$^5$)$_n$—CO— (=W) is AHCP;

(d) Iad to Iid, Iaad to Iiad, Iabd to Iibd, Iacd to Iicd, Iaabd to Iiabd, Iaacd to Iiacd, Iabcd to Iibcd and Iaabcd to Iiabcd, which correspond to the formulae Ia to Ii, Iaa to Iia, Iab to Iib, Iac to Iic, Iaab to Iiab, Iaac to Iiac, Iabc to Iibc and Iaabc to Iiabc but in which additionally E is Ile or Leu;

Particularly preferred compounds are those of the part-formulae:

I* and Ia* to Ii*, which correspond to the formulae I and Ia to Ii, as well as those compounds which correspond to the other abovementioned part-formulae but in which additionally
  Q is NH,
  Y is H, A or —CH$_2$R$^{11}$ and
  R$^{11}$ is o-, m- or p-aminomethylbenzyl, o-, m- or p-guanidinomethylbenzyl, 3-pyridyl, 4-amino-2-methyl-5-pyrimidinyl or 2-amino-5,6-dimethyl-3-pyrazinyl;

I' and Ia' to Ii', which correspond to the formulae I and Ia to Ii, as well as those compounds which correspond to the other abovementioned part-formulae but in which additionally Q is NH and Y is H, A, 4-amino-2-methyl-5-pyrimidinylmethyl or 2-amino-5,6-dimethyl-3-pyrazinylmethyl.

Another particularly preferred group of compounds corresponds to formula I wherein $R^1$ is $R^6R^7N$—, $R^6OOC$— or $R^6$—O—(CH$_2$C-H$_2$O)$_r$—;

—NH—CHR$^2$—CO— is Leu, Mal, p-F-Phe, Phe, D-Phe, 3-Pya, 2-Tia, Tyr or D-Tyr;

—Z—C$_m$H$_{2m}$—CO— is βAla or Gly;

$R^3$ is isobutyl, benzyl or cyclohexylmethyl;

$R^4$ is (H, OH);

—(CHR$^5$)$_n$— is —CH$_2$—, —CH$_2$CH$_2$— or —CH$_2$—CHA—;

E is missing or is Ala, Gly, Ile, Leu, Nle or Ile-Val;

Q—Y is OH, OA, NHA, NH—C$_t$H$_{2t}$—R$^{11}$, NH—C$_t$H$_{2t}$—OH or NH—C$_t$H$_{2t}$—NA$_2$;

$R^6$ and $R^7$ are each independently H or A;

$R^7$ is also $R^9$—O—CO—;

$R^9$ is A or benzyl;

$R^6R^7N$ is also a piperidinyl, morpholinyl, piperazinyl or pyrrolidinyl group which is unsubstituted or substituted by A, OH, NH$_2$, NHA, NA$_2$, NH—CO—A, NH—CO—OA, NH—SO$_2$—A, hydroxyalkyl, COOH, COOA, NH—CO—NH$_2$, NH—CO—NHA or guanidinyl;

$R^{11}$ is p-aminosulfonylphenyl, 1-benzyl-4-piperidinyl, 3-pyridyl, 4-amino-2-methyl-5-pyrimidinyl, 2-amino-5,6-dimethyl-3-pyrazinyl or 5-tetrazolyl;

y is 0 or 1;

p is 0, 1, 2, 3, 4, 5, 6 or 7;

r is 1 or 2;

t is 1, 2, 3, 4 or 5;

-alkyl- is an alkylene group having 1–8 C atoms; and

A is alkyl having 1–8 C atoms;

and physiologically acceptable salts thereof.

Among these compounds, particularly preferred are those wherein the group —Z—C$_m$H$_{2m}$—CO stands for βAla.

The compounds of the formula I, as well as the starting materials for the preparation thereof, are furthermore prepared by methods which are known per se and as are described in the literature (for example in the standard works such as Houben-Weyl, Methoden der organischen Chemie, 1974 (Methods of Organic Chemistry), published by Georg Thieme, Stuttgart; as well as EP-A 45665, EP-A 77028, EP-A 77029, EP-A 81793, EP-A 249096) specifically under reaction conditions which are known and suitable for the said reactions. In this connection it is also possible to make use of variants which are known per se and which are not mentioned in detail herein.

It is also possible, if desired, to form the starting materials in situ so that they are not isolated from the reaction mixture but are immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which correspond to the formula I apart from containing, in place of one or more free amino and/or hydroxyl groups, corresponding protected amino and/or hydroxyl groups, preferably those which carry an amino protective group in place of an H atom bonded to an N atom, for example those which correspond to the formula I but contain in place of a His group an N(im)-R'-His group (in which R' is an amino protective group, for example BOM or DNP), or those of the formula $R^1$—C$_p$H$_{2p}$—(NH)$_y$—CO—NH—CH-R$^2$—CO—Z—C$_m$H$_{2m}$—CO—NH—CH-R$^3$—CH(NHR')—(CHR$^5$)$_n$—CO—E—Q—Y.

Further preferred starting materials are those which carry, in place of the H atom of a hydroxyl group, a hydroxyl protective group, for example those of the formula $R^1$—C$_p$H$_{2p}$—(NH)$_y$—CO—NH—CH-R$^2$—CO—Z—C$_m$H$_{2m}$—CO—NH—CHR$^3$—CHOR'-'—(CHR$^5$)$_n$—CO—E—Q—Y, in which R" is a hydroxyl protective group.

It is also possible for more than one—identical or different—protected amino and/or hydroxyl groups to be present in the molecule of the starting material. If the protective groups which are present differ from one another it is possible in many cases to eliminate them selectively.

The term "amino protective group" is generally known and relates to groups which are suitable for protecting (blocking) an amino group from chemical reactions but which can easily be removed after the desired chemical reaction has been carried out elsewhere in the molecule. Typical of such groups are, in particular, unsubstituted or substituted acyl, aryl (for example DNP), aralkoxymethyl (for example BOM) or aralkyl groups (for example benzyl, 4-nitrobenzyl, triphenylmethyl). Since the amino protective groups are removed after the desired reaction (or reaction sequence), their nature and size are not otherwise critical; however, those which are preferred have 1–20, in particular 1–8, C atoms. The term "acyl group" in connection with the present process is to be interpreted in the widest sense. It embraces acyl groups derived from aliphatic, araliphatic, aromatic or heterocyclic carboxylic acids or sulfonic acids, as well as, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ETOC, 2,2,2trichloroethoxycarbonyl, IPOC, BOC, 2-iodoethoxycarbonyl; aralkyloxycarbonyl such as CBZ, 4-methoxybenzyloxycarbonyl, FMOC. Preferred amino protective groups are BOC, DNP and BOM, as well as CBZ, FMOC, benzyl and acetyl.

The term "hydroxyl protective group" is likewise generally known and relates to groups which are suitable for protecting a hydroxyl group from chemical reactions but which can easily be removed after the desired chemical reaction has been carried out elsewhere in the molecule. Typical of such groups are the abovementioned unsubstituted or substituted aryl, aralkyl or acyl groups, as well as alkyl groups. The nature and size of the hydroxyl protective groups are not critical because they are removed again after the desired chemical reaction or reaction sequence; preferred groups have 1–20, in particular 1–10, C atoms. Examples of hydroxyl protective groups are, inter alia, tert.-butyl, benzyl, p-nitrobenzoyl, p-toluenesulphonyl and acetyl, with benzyl and acetyl being particularly preferred.

The functional derivatives of the compounds of the formula I which are to be used as starting materials can be prepared by customary methods of amino acid and peptide synthesis as are described, for example, in the said standard works and patent applications, for example also by the solid-phase method of Merrifield.

The liberation of the compounds of the formula I from their functional derivatives is effected—depending on the protective group used—for example with strong acids, preferably with trifluoroacetic acid or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary. Suitable and preferred inert solvents are organic, for example carboxylic acids such as acetic acid, ethers such as tetrahydrofuran or dioxane, amides such as dimethylformamide (DMF), halogenated hydrocarbons such as dichloromethane, as well as alcohols such as methanol, ethanol or isopropanol, and water. Furthermore suitable are mixtures of the abovementioned solvents. Trifluoroacetic acid is preferably used in excess without the addition of another solvent, and perchloric acid in the form of a mixture of acetic acid and 70% perchloric acid in the ratio 9:1. The reaction temperatures for the cleavage are preferably between about 0° and about 50°, preferably between 15° and 30° (room temperature).

The BOC group can be eliminated, for example, preferably with 40% trifluoroacetic acid in dichloromethane or with about 3 to 5N HCl in dioxane at 15°–30°, and the FMOC group with an approximately 5–20% solution of dimethylamine, diethylamine or piperidine in DMF at 15°–30°. Elimination of the DNP group is effected, for example, also with an approximately 3–10% solution of 2-mercaptoethanol in DMF/water at 15°–30°.

Protective groups which can be removed by hydrogenolysis (for example BOM, CBZ or benzyl) can be eliminated, for example by treatment with hydrogen in the presence of a catalyst (for example a noble metal catalyst such as palladium, preferably on a support such as carbon). Solvents suitable for this are those mentioned above, in particular, for example, alcohols such as methanol or ethanol or amides such as DMF. Hydrogenolysis is, as a rule, carried out at temperatures between about 0° and 100° under pressures between about 1 and 200 bar, preferably at 20°–30° and under 1–10 bar. Hydrogenolysis of the CBZ group is effected satisfactorily, for example, on 5–10% Pd—C in methanol at 20°–30°.

Compounds of the formula I can also be obtained by direct peptide synthesis from a carboxylic acid component (formula II) and an amine component (formula III). Examples of suitable carboxylic acid components are those of the part-formulae (a) $R^1$—$C_pH_{2p}$—(NH)$_y$—COOH, (b) $R^1$—$C_pH_{2p}$—(NH)$_y$—CO—NH—CHR$^2$—COOH, (c) $R^1$—$C_pH_{2p}$—(NH)$_y$—CO—NH—CHR$^2$—CO—Z—$C_mH_{2m}$—COOH, (d) $R^1$—$C_pH_{2p}$—(NH)$_y$—CO—NH—CHR$^2$—CO—Z—$C_mH_{2m}$—CO—W—OH or (f) $R^1$—$C_pH_{2p}$—(NH)$_y$—CO—NH—CHR$^2$—CO—Z—$C_mH_{2m}$CO—W—E—OH, and of amine components are those of the part-formulae (a) H$_2$N—CHR$^2$—CO—Z—$C_mH_{2m}$—CO—W—E—Q—Y, (b) H—Z—$C_mH_{2m}$—CO—W—E—Q—Y, (c) H—W—E—Q—Y, (d) H—E—Q—Y or (f) H—NR$^{10}$—Y. The peptide linkage can, however, also be formed within the group E; this entails a carboxylic acid of the formula (e) $R^1$—$C_pH_{2p}$—(NH)$_y$—CO—NH—CHR$^2$—CO—Z—$C_mH_{2m}$—CO—W—E$^1$—OH being reacted with an amino compound of the formula H—E$^2$—Q—Y, where E$^1$+E$^2$=E. The methods preferably used for this are those customary in peptide synthesis, as are described, for example, in Houben-Weyl, l. c., Volume 15/II, pages 1–806 (1974).

The reaction is preferably effected in the presence of a dehydrating agent, for example a carbodiimide such as DCCI or dimethylaminopropylethyl-carbodiimide, or else propanephosphonic anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, or a nitrile such as acetonitrile, at temperatures between about −10 and 40, preferably between 0° and 30°.

It is also possible, in place of II or III, to use suitable reactive derivatives of these substances in the reaction, for example those in which reactive groups have undergone intermediate blocking with protective groups. The acid derivatives II can be used, for example, in the form of their activated esters which are preferably formed in situ, for example by addition of HOBt or N-hydroxysuccinimide.

Urea derivatives of the formula I (y=1) can be obtained, for example, by reacting an isocyanate of the formula $R^1$—$C_pH_{2p}$—NCO (can be prepared from an amine of the formula $R^1$—$C_pH_{2p}$—NH$_2$ and phosgene) with an amine of the formula H$_2$N—CHR$^2$—CO—Z—$C_mH_{2m}$—CO—W—E—Q—Y (IIa), preferably in an inert solvent such as THF, at temperatures between about −10° and 40°, preferably between 10° and 30°.

The starting materials of formulae II and III are mostly known. Those which are unknown can be prepared by known methods, for example the abovementioned methods of peptide synthesis and of elimination of protective groups.

If desired, it is possible for a functionally modified amino and/or hydroxyl group in a compound of the formula I to be liberated by solvolysis or hydrogenolysis by one of the methods described above.

Thus, for example, a compound of the formula I which contains an $R^9$—$C_xH_{2x}$—O—CO—NH—, an AcNH—, an ArCH$_2$—SO$_3$— or an AOOC-group can be converted into the corresponding compound of the formula I which contains in its stead an H$_2$N—, an HSO$_3$— or an HOOC-group, preferably by selective solvolysis by one of the methods indicated above. AOOC-groups can, for example, be hydrolyzed with NaOH or KOH in water/dioxane at temperatures between 0° and 40°, preferably 10° and 30°.

Furthermore, for example, keto compounds of the formula I ($R^4$=O) can be reduced to compounds of the formula I ($R^4$=(H, OH)), for example with a complex metal hydride such as NaBH$_4$ which does not simultaneously reduce the peptide carbonyl groups, in an inert solvent such as methanol at temperatures between about −10° and +30°.

Keto compounds of the formula I ($R^4$=O) can also be converted into compounds of the formula I ($R^4$=H, NH$_2$) by reductive amination. The reductive amination can be carried out in one or more stages. Thus, for example, the keto compound can be treated with ammonium salts, for example ammonium acetate and NaCNBH$_3$, preferably in an inert solvent, for example an alcohol such as methanol, at temperatures between about 0° and 50°, in particular between 15° and 30°. It is furthermore possible initially to convert the keto compound into the oxime, using hydroxylamine in a customary manner, and to reduce the oxime to the amine, for example by catalytic hydrogenation on Raney nickel. A base of the formula I can be converted into the relevant acid addition salt using an acid. Particularly suitable acids for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and lauryl sulfuric acid. Salts with physiologically unacceptable acids, for example picrates, can be used to isolate and/or purify the compounds of the formula I.

The new compounds of the formula I and the physiologically acceptable salts thereof can be used to prepare pharmaceutical products by converting them, together with at least one vehicle or auxiliary and, if desired, together with one or more other active substance(s), into a suitable dosage form. The compositions obtained in this way can be used as medicaments in human or veterinary medicine. Suitable vehicles are organic or inorganic substances which are suitable for enteral (for example oral or rectal) or parenteral administration or for administration in the form of a spray for inhalation and which do not react with the new compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Used orally are, in particular, tablets, coated tablets, capsules, syrups, elixirs or drops; specifically of interest are lacquered tablets and capsules with enteric coatings or capsule shells. Used rectally are suppositories, and for parenteral administration are solutions, preferably oily or aqueous solutions, as well as suspensions, emulsions or implants. For administration by spray for inhalation, it is possible to use sprays which contain the active substance either dissolved or suspended in a propellant gas mixture (for example fluorochlorohydrocarbons). The active substance is preferably used for this in micronized form, with one or more additional physiologically tolerated solvents possibly being present, for example ethanol. Solutions for inhalation can be administered with the aid of customary inhalers. The new compounds can also be freeze-dried and the resulting lyophilizates used, for example, to prepare products for injection. The stated compositions can be sterilized and/or contain auxiliaries such as preservatives, stabilizers and/or wetting agents, emulsifiers, salts to influence the osmotic pressure, buffer substances, colorants and/or flavorings. They can, if desired, also contain one or more other active substances, for example one or more vitamins.

The substances according to the invention are, as a rule, administered in analogy to other known, commercially available peptides, but especially in analogy to the compounds described in EP-A 249096, preferably in dosages between about 10 mg and 1 g, in particular between 50 mg and 500 mg, per dosage unit. The daily dosage is preferably between about 0.2 and 20 mg/kg, in particular 1 and 10 mg/kg, of bodyweight. The specific dose for each particular patient depends, however, on a wide variety of factors, for example on the activity of the specific compound used, on the age, body weight, general state of health and sex, on the diet, on the time and route of administration and on the rate of excretion, medicinal substance combination and severity of the particular disease for which the therapy is applied. Parenteral administration is preferred.

Renin-dependent hypertension and hyperaldosteronism can be effectively treated by administration of dosages between, in particular, about 1 and 300, preferably between 5 and 50, mg/kg of body weight. For diagnostic purposes, it is possible and preferable for the new compounds to be administered in single doses, particularly in about 0.1 and 10 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, and of corresponding German application P 38 12 328.2, are hereby incorporated by reference.

EXAMPLES

In the examples which follow, "usual working up" means: if necessary, water is added, the pH is adjusted to between 2 and 8, depending on the constitution of the final product, extraction is carried out with ethyl acetate or dichloromethane, the organic phase is separated off, dried over sodium sulfate, filtered and concentrated, and purification is carried out by chromatography on silica gel and/or crystallization.

EXAMPLE 1

A mixture of 890 mg of 3S-hydroxy-4S-(4-dimethylaminobutyryl-L-phenylalanyl-glycyl-amino)-5-cyclohexyl-pentanoyl-N-imi-(2,4-dinitrophenyl)-L-histidine N-butylamide ["4-dimethylaminobutyryl-Phe-Gly-AHCP-(imi-DNP-His) N-butylamide"; obtainable by reaction of 4-dimethylaminobutric acid with H-Phe-Gly-AHCP-(imi-DNP-His) N-butylamide], 2 g of 2-mercaptoethanol, 20 ml of DMF and 20 ml of water is adjusted to pH 8 with aqueous Na$_2$CO$_3$ solution while stirring at 20° and is stirred at 20° for 2 hours. The usual working up results in 4-dimethylaminobutyryl-Phe-Gly-AHCP-His N-butylamide.

EXAMPLE 2

10 g of 3S-CBZ-amino-4S-(4-dimethylamino-butyryl-Phe-Gly-amino)-5-cyclohexyl-pentanoyl-Ile AMPA (obtainable by reaction of 4-dimethylaminobutyryl-Phe-OH with 3S-CBZ-amino-4S-Gly-amino-5-cyclohexyl-pentanoyl-Ile AMPA) are dissolved in 150 ml of ethanol and hydrogenated on 5 g of 10% Pd-C at 20° and under 1 bar until $H_2$ uptake ceases, the mixture is filtered, the filtrate is evaporated, and purification by chromatography results in 3S-amino-4S-(4-dimethylamino-butyryl-Phe-Gly-amino)-5-cyclohexyl-pentanoyl-Ile AMPA ("4-dimethylaminobutyryl-Phe-Gly-DACP-Ile AMPA").

The following are obtained analogously from the corresponding CBZ derivatives:
4-Morpholino-butyryl-Phe-Gly-DACH-Ile-OMe
4-Pyrrolidino-butyryl-Phe-Gly-DAMH-Ile-$NH_2$
4-Piperidino-butyryl-Phe-Gly-DAPP-Ile-OEt.

4-BOC-amino-piperidinocarbonyl-Phe-Gly-AHCP-His-$NH_2$ is obtained analogously by hydrogenolysis of 4-BOC-aminopiperidinocarbonyl-Phe-Gly-AHCP-(imiBOM-His) amide.

EXAMPLE 3

A solution of 1 g of the di-BOC derivative of 4-guanidino-piperidinocarbonyl-Phe-βAla-AHCP-Ile AMPA [obtainable by reaction of N,N'-di-BOC-S-methyl-isothiourea (m.p. 121°) with 4-aminopiperidinocarbonyl-Phe benzyl ester to give 4-(N,N'-di-BOC-guanidino)-piperidinocarbonyl-Phe benzyl ester, hydrogenolysis to give 4-(N,N'-di-BOC-guanidino)-piperidinocarbonyl-Phe-OH and condensation with H-βAla-AHCP-Ile AMPA] in 20 ml of 4N HCL in dioxane is stirred at 20° for 30 min and then evaporated. 4-Guanidino-piperidinocarbonyl-Phe-βAla-AHCP-Ile AMPA is obtained in the form of the dihydrochloride.

The following are obtained analogously from the corresponding di-BOC or tri-BOC derivatives:
4-Guanidino-piperidinocarbonyl-Phe-Gly-AHCP-Ile AMPA
4-Guanidino-piperidinocarbonyl-Phe-Gly-AHCP-Ile ADPA
4-Guanidino-piperidinocarbonyl-Phe-Gly-AHCP-Leu AMPA
4-Guanidino-piperidinocarbonyl-Phe-Gly-AHCP-Leu ADPA
4-Guanidino-piperidinocarbonyl-Phe-βAla-AHCP-Ile ADPA
4-Guanidino-piperidinocarbonyl-Phe-βAla-AHCP-Leu AMPA
4-Guanidino-piperidinocarbonyl-Phe-βAla-AHCP-Leu ADPA
6-Guanidino-hexanoyl-Phe-Gly-AHCP-Ile AMPA
6-Guanidino-hexanoyl-Phe-Gly-AHCP-Ile ADPA
6-Guanidino-hexanoyl-Phe-Gly-AHCP-Leu AMPA
6-Guanidino-hexanoyl-Phe-Gly-AHCP-Leu ADPA
6-Guanidino-hexanoyl-Phe-βAla-AHCP-Ile AMPA
6-Guanidino-hexanoyl-Phe-βAla-AHCP-Ile ADPA
6-Guanidino-hexanoyl-Phe-βAla-AHCP-Leu AMPA
6-Guanidino-hexanoyl-Phe-βAla-AHCP-Leu ADPA
6-Guanidino-hexanoyl-Mal-Gly-AHCP-Ile AMPA
6-Guanidino-hexanoyl-Mal-Gly-AHCP-Ile ADPA
6-Guanidino-hexanoyl-Mal-βAla-AHCP-Ile AMPA
6-Guanidino-hexanoyl-Mal-βAla-AHCP-Ile ADPA.
6-Amino-hexanoyl-Phe-Gly-AHCP-Ile N-6-aminohexyl-amide
6-Amino-hexanoyl-Phe-βAla-AHCP-Ile N-6-aminohexyl-amide
6-Amino-hexanoyl-Phe-Gly-AHCP-Ile N-6-guanidinohexyl-amide
6-Amino-hexanoyl-Phe-βAla-AHCP-Ile N-6-guanidinohexyl-amide.

EXAMPLE 4

1.01 g of N-methylmorpholine are added to a solution of 6.52 g of H-Phe-Gly-AHCP-Ile AMPA (obtainable by condensation of BOC-Phe-Gly-AHCP-Ile-OH with 4-amino-5-aminomethyl-2-methyl-pyrimidine to give BOC-Phe-Gly-AHCP-Ile AMPA and subsequent elimination of the BOC group) in 160 ml of DMF. While stirring, 2.31 g of 6-BOC-aminohexanoic acid, 1.35 g of HOBt and a solution of 2.06 g of DCCI in 50 ml of $CH_2Cl_2$ are added, the mixture is stirred at 4° for 12 hours, the precipitated dicyclohexylurea is filtered off, and the filtrate is evaporated. The usual working up results in 6-BOC-aminohexanoyl-Phe-Gly-AHCP-Ile AMPA, m.p. 114°.

The following are obtained analogously:
BOC-βAla-Phe-Gly-AHCP-Ile-$NH_2$
BOC-βAla-Phe-Gly-AHCP-Ile N-butylamide
BOC-βAla-Phe-Gly-AHCP-Ile N-pentylamide
BOC-βAla-Phe-Gly-AHCP-Ile N,N-diethylamide
BOC-βAla-Phe-Gly-AHCP-Ile AMPA
BOC-βAla-Phe-Gly-AHCP-Ile ADPA
BOC-βAla-Phe-Gly-AHCP-Leu AMPA
BOC-βAla-Phe-Gly-AHCP-Leu ADPA
BOC-βAla-Phe-βAla-AHCP-Ile AMPA
BOC-βAla-Phe-βAla-AHCP-Ile ADPA
BOC-βAla-Phe-βAla-AHCP-Leu AMPA
BOC-βAla-Phe-βAla-AHCP-Leu ADPA
4-BOC-aminobutyryl-Phe-Gly-AHCP-Ile AMPA
4-BOC-aminobutyryl-Phe-Gly-AHCP-Ile ADPA
4-BOC-aminobutyryl-Phe-Gly-AHCP-Leu AMPA
4-BOC-aminobutyryl-Phe-Gly-AHCP-Leu ADPA
4-BOC-aminobutyryl-Phe-βAla-AHCP-Ile AMPA
4-BOC-aminobutyryl-Phe-βAla-AHCP-Ile ADPA
4-BOC-aminobutyryl-Phe-βAla-AHCP-Lue AMPA
4-BOC-aminobutyryl-Phe-βAla-AHCP-Lue ADPA
4-BOC-aminobutyryl-Mal-Gly-AHCP-Ile AMPA
4-BOC-aminobutyryl-Mal-Gly-AHCP-Ile ADPA
4-BOC-aminobutyryl-Mal-βAla-AHCP-Ile AMPA
4-BOC-aminobutyryl-Mal-βAla-AHCP-Ile ADPA
5-BOC-aminopentanoyl-Phe-Gly-AHCP-Ile AMPA
5-BOC-aminopentanoyl-Phe-Gly-AHCP-Ile ADPA
5-BOC-aminopentanoyl-Phe-βAla-AHCP-Ile AMPA
5-BOC-aminopentanoyl-Phe-βAla-AHCP-Ile ADPA
6-BOC-aminohexanoyl-Phe-Gly-AHCP-Ile amide
6-BOC-aminohexanoyl-βAla-Gly-AHCP-Ile amide
6-BOC-aminohexanoyl-Phe-Gly-AHCP-Ile ADPA, m.p. 170°–171°
6-BOC-aminohexanoyl-Phe-Gly-AHCP-Leu AMPA
6-BOC-aminohexanoyl-Phe-Gly-AHCP-Leu ADPA
6-BOC-aminohexanoyl-Phe-βAla-AHCP-Ile AMPA
6-BOC-aminohexanoyl-Phe-βAla-AHCP-Ile ADPA
6-BOC-aminohexanoyl-Phe-βAla-AHCP-Leu AMPA
6-BOC-aminohexanoyl-Phe-βAla-AHCP-Leu ADPA
6-BOC-aminohexanoyl-Mal-Gly-AHCP-Ile AMPA
6-BOC-aminohexanoyl-Mal-Gly-AHCP-Ile ADPA
6-BOC-aminohexanoyl-Mal-βAla-AHCP-Ile AMPA
6-BOC-aminohexanoyl-Mal-βAla-AHCP-Ile ADPA
6-BOC-aminohexanoyl-Phe-Gly-AHCP-Ile N-3-pyridylmethylamide m.p. 167°–168°
6-BOC-aminohexanoyl-Phe-βAla-AHCP-Ile N-3-pyridylmethylamide 6-BOC-aminohexanoyl-Phe-Gly-AHCP-Ile N-m-aminomethyl-benzylamide
6-BOC-aminohexanoyl-Phe-βAla-AHCP-Ile N-m-aminomethyl-benzylamide
6-BOC-aminohexanoyl-Phe-Gly-AHCP-Ile N-p-dimethylaminomethyl-benzylamide
6-BOC-aminohexanoyl-Phe-βAla-AHCP-Ile N-p-dimethylaminomethyl-benzylamide
6BOC-aminohexanoyl-Phe-Gly-AHCP-Ile N-5-tetrazolylmethylamide
6-BOC-aminohexanoyl-Phe-βAla-AHCP-Ile N-5tetrazolylmethylamide
6-BOC-aminohexanoyl-Phe-Gly-AHCP-Ile N-3dimethylaminopropylamide
6-BOC-aminohexanoyl-Phe-βAla-AHCP-Ile N-3dimethylaminopropylamide
6-BOC-aminohexanoyl-Phe-Gly-AHCP-Ile N-2-sulfoethylamide
6-BOC-aminohexanoyl-Phe-βAla-AHCP-Ile N-2-sulfoethylamide
3-[6-BOC-aminohexanoyl-Phe]-propionyl-AHCP-Ile AMPA
3-[6-BOC-aminohexanoyl-Phe]-propionyl-AHCP-Ile ADPA
4-[6-BOC-aminohexanoyl-Phe]-3-thiabutyryl-AHCP-Ile AMPA
4-[6-BOC-aminohexanoyl-Phe]-3-thiabutyryl-AHCP-Ile ADPA
7-BOC-aminoheptanoyl-Phe-Gly-AHCP-Ile AMPA
7-BOC-aminoheptanoyl-Phe-Gly-AHCP-Ile ADPA
7-BOC-aminoheptanoyl-Phe-Gly-AHCP-Ile AMPA
7-BOC-aminoheptanoyl-Phe-Gly-AHCP-Ile ADPA
8-BOC-aminooctanoyl-Phe-Gly-AHCP-Ile AMPA, m.p. 162°
8-BOC-aminooctanoyl-Phe-Gly-AHCP-Ile ADPA
8-BOC-aminooctanoyl-Phe-βAla-AHCP-Ile AMPA, m.p. 203° (dec.)
8-BOC-aminooctanoyl-Phe-βAla-AHCP-Ile ADPA
Dimethylaminoacetyl-Phe-Gly-AHCP-Ile AMPA
3-Dimethylamino-propionyl-Phe-Gly-AHCP-Ile AMPA
4-Dimethylamino-butyryl-Phe-Gly-AHCP-Ile AMPA, m.p. 198°–199°; dihydrochloride m.p. 131° (decomposition)
4-Dimethylamino-butyryl-Phe-Gly-AHCP-Ile ADPA, dihydrochloride m.p. 131°
4-Dimethylamino-butyryl-Phe-Gly-AHCP-Ile p-sulfamoylanilide, hydrochloride m.p. 136°–140°
4-Dimethylamino-butyryl-Phe-Gly-AHCP-Leu AMPA
4-Dimethylamino-butyryl-Phe-Gly-AHCP-Leu ADPA
4-Dimethylamino-butyryl-Phe-βAla-AHCP-Ile AMPA, dihydrochloride m.p. 196° (decomposition)
4-Dimethylamino-butyryl-Phe-βAla-AHCP-Ile ADPA
4-Dimethylamino-butyryl-Phe-βAla-AHCP-Ile AMPA
4-Dimethylamino-butyryl-Phe-βAla-AHCP-Leu ADPA
4-Dimethylaminobutyryl-Mal-Gly-AHCP-Ile AMPA
4-Dimethylaminobutyryl-Mal-Gly-AHCP-Ile ADPA
4-Dimethylaminobutyryl-Mal-βAla-AHCP-Ile AMPA
4-Dimethylaminobutyryl-Mal-βAla-AHCP-Ile ADPA
5-Dimethylamino-pentanoyl-Phe-Gly-AHCP-Ile AMPA
5-Dimethylamino-pentanoyl-Phe-Gly-AHCP-Ile ADPA
5-Dimethylamino-pentanoyl-Phe-Gly-AHCP-Leu AMPA
5-Dimethylamino-pentanoyl-Phe-Gly-AHCP-Leu ADPA
5-Dimethylamino-pentanoyl-Phe-βAla-AHCP-Ile AMPA
5-Dimethylamino-pentanoyl-Phe-βAla-AHCP-Ile ADPA
5-Dimethylamino-pentanoyl-Phe-βAla-AHCP-Leu AMPA
5-Dimethylamino-pentanoyl-Phe-βAla-AHCP-Leu ADPA
6-Dimethylamino-hexanoyl-Phe-Gly-AHCP-Ile AMPA
6-Dimethylamino-hexanoyl-Phe-Gly-AHCP-Ile ADPA
6-Dimethylamino-hexanoyl-Phe-Gly-AHCP-Leu AMPA
6-Dimethylamino-hexanoyl-Phe-Gly-AHCP-Leu ADPA
6-Dimethylamino-hexanoyl-Phe-βAla-AHCP-Ile AMPA
6-Dimethylamino-hexanoyl-Phe-βAla-AHCP-Ile ADPA
6-Dimethylamino-hexanoyl-Phe-βAla-AHCP-Leu AMPA
6-Dimethylamino-hexanoyl-Phe-βAla-AHCP-Leu ADPA
3-[6-Dimethylamino-hexanoyl-Phe]-propionyl-AHCP-Ile AMPA
3-[6-Dimethylamino-hexanoyl-Phe]-propionyl-AHCP-Ile ADPA
3-[6-Dimethylamino-hexanoyl-Phe]-3-thiabutyryl-AHCP-Ile AMPA
4-[6-Dimethylamino-hexanoyl-Phe]-3-thiabutyryl-AHCP-Ile ADPA
6-Dimethylamino-hexanoyl-Mal-Gly-AHCP-Ile AMPA
6-Dimethylamino-hexanoyl-Mal-Gly-AHCP-Ile ADPA
6-Dimethylamino-hexanoyl-Mal-βAla-AHCP-Ile AMPA
6-Dimethylamino-hexanoyl-Mal-βAla-AHCP-Ile ADPA
7-Dimethylamino-heptanoyl-Phe-Gly-AHCP-Ile AMPA
8-Dimethylamino-octanoyl-Phe-Gly-AHCP-Ile AMPA
(4-Piperidyl)-acetyl-Phe-Gly-AHCP-Ile AMPA, dihydrochloride m.p. 232°
(4-Piperidyl)-acetyl-Phe-Gly-AHCP-Ile ADPA
(4-Piperidyl)-acetyl-Phe-βAla-AHCP-Ile AMPA, dihydrochloride m.p. 75°
(4-Piperidyl)-acetyl-Phe-βAla-AHCP-Ile ADPA
Piperidinoacetyl-Phe-Gly-AHCP-Ile AMPA
Piperidinoacetyl-Phe-Gly-AHCP-Ile ADPA
Piperidinoacetyl-Phe-βAla-AHCP-Ile AMPA
Piperidinoacetyl-Phe-βAla-AHCP-Ile ADPA
3-Piperidino-propionyl-Phe-Gly-AHCP-Ile AMPA
3-Piperidino-propionyl-Phe-Gly-AHCP-Ile ADPA
3-Piperidino-propionyl-Phe-βAla-AHCP-Ile AMPA, m.p. 188°
3-Piperidino-propionyl-Phe-βAla-AHCP-Ile ADPA
4-Pyrrolidino-butyryl-Phe-Gly-AHCP-Ile AMPA, dihydrochloride, oil
4-Pyrrolidino-butyryl-Phe-Gly-AHCP-Ile ADPA
4-Pyrrolidino-butyryl-Phe-βAla-AHCP-Ile AMPA
4-Pyrrolidino-butyryl-Phe-βAla-AHCP-Ile ADPA
4-Piperidino-butyryl-Phe-Gly-AHCP-Ile AMPA, dihydrochloride m.p. 79°

4-Piperidino-butyryl-Phe-Gly-AHCP-Ile ADPA
4-Piperidino-butyryl-Phe-βAla-AHCP-Ile AMPA, m.p. 199°
4-Piperidino-butyryl-Phe-βAla-AHCP-Ile ADPA
5-Pyrrolidino-pentanoyl-Phe-Gly-AHCP-Ile AMPA, dihydrochloride, oil
5-Pyrrolidino-pentanoyl-Phe-Gly-AHCP-Ile ADPA
5-Pyrrolidino-pentanoyl-Phe-βAla-AHCP-Ile AMPA, m.p. 231°
5-Pyrrolidino-pentanoyl-Phe-βAla-AHCP-Ile ADPA
5-Piperidino-pentanoyl-Phe-Gly-AHCP-Ile AMPA, dihydrochloride m.p. 62°
5-Piperidino-pentanoyl-Phe-Gly-AHCP-Ile ADPA
5-Piperidino-pentanoyl-Phe-βAla-AHCP-Ile AMPA, m.p. 202°
5-Piperidino-pentanoyl-Phe-βAla-AHCP-Ile ADPA
6-CBZ-amino-hexanoyl-Phe-Gly-AHCP-Ile AMPA,
6-CBZ-amino-hexanoyl-Phe-Gly-AHCP-Ile ADPA, m.p. 167°-168° (decomposition)
6-CBZ-amino-hexanoyl-Phe-βAla-AHCP-Ile AMPA
6-CBZ-amino-hexanoyl-Phe-βAla-AHCP-Ile ADPA
2-CBZ-amino-2-methyl-propionyl-Phe-Gly-AHCP-Ile AMPA, m.p. 128°
2-CBZ-amino-2-methyl-propionyl-Phe-Gly-AHCP-Ile ADPA
2-CBZ-amino-2-methyl-propionyl-Phe-βAla-AHCP-Ile AMPA, m.p. 191°-192°
2-CBZ-amino-2-methyl-propionyl-Phe-βAla-AHCP-Ile ADPA
2-CBZ-amino-2-methyl-propionyl-Mal-Gly-AHCP-Ile AMPA, m.p. 185°-186°
2-CBZ-amino-2-methyl-propionyl-Mal-Gly-AHCP-Ile ADPA
2-CBZ-amino-2-methyl-propionyl-Mal-βAla-AHCP-Ile AMPA, m.p. 191°-192°
2-CBZ-amino-2-methyl-propionyl-Mal-βAla-AHCP-Ile ADPA.

Example 5

4-BOC-amino-piperidinocarbonyl-Phe-βAla-AHCP-Ile AMPA is obtained in analogy to Example 4 from 4-BOC-amino-piperidinocarbonyl-Phe-OH (m.p. 158°-159°) and H-βAla-AHCP-Ile AMPA (obtainable from BOC-βAla-AHCP-Ile AMPA (m.p. 163°-164°)), m.p. 185° (decomposition).

The following are obtained analogously
3,6-Dioxaheptanoyl-Phe-Gly-AHCP-Ile AMPA, m.p. 130° [obtainable via BOC-Gly-AHCP-Ile AMPA (m.p. 151°) and H-Gly-AHCP-Ile AMPA]
3,6-Dioxaheptanoyl-Phe-Gly-AHCP-Ile ADPA
3,6-Dioxaheptanoyl-Phe-βAla-AHCP-Ile AMPA
3,6-Dioxaheptanoyl-Phe-βAla-Ile ADPA
3,6,9-Trioxadecanoyl-Phe-Gly-AHCP-Ile AMPA, m.p. 110°; hydrochloride m.p. 85°
3,6,9-Trioxadecanoyl-Phe-Gly-AHCP-Ile ADPA
3,6,9-Trioxadecanoyl-Phe-βAla-AHCP-Ile AMPA
3,6,9-Trioxadecanoyl-Phe-βAla-AHCP-Ile ADPA
4-BOC-amino-piperidinocarbonyl-Phe-Gly-AHCP-Ile AMPA, m.p. 152°-153°
4-BOC-amino-piperidinocarbonyl-Phe-Gly-AHCP-Ile ADPA
4-BOC-amino-piperidinocarbonyl-Phe-Gly-AHCP-Leu AMPA
4-BOC-amino-piperidinocarbonyl-Phe-Gly-AHCP-Leu ADPA
4-BOC-amino-piperidinocarbonyl-Phe-βAla-AHCP-Ile AMPA
4-BOC-amino-piperidinocarbonyl-Phe-βAla-AHCP-Ile ADPA, m.p. 173°-174°
4-BOC-amino-piperidinocarbonyl-Phe-βAla-AHCP-Ile N-2-pyridylmethylamide
4-BOC-amino-piperidinocarbonyl-Phe-βAla-AHCP-Ile N-3-pyridylmethylamide, m.p. 145°
4-BOC-amino-piperidinocarbonyl-Phe-βAla-AHCP-Leu AMPA, m.p. 181°-182°
4-BOC-amino-piperidinocarbonyl-Phe-βAla-AHCP-Leu ADPA
4-BOC-amino-piperidinocarbonyl-Phe-Gly-AHCH-Ile AMPA
4-BOC-amino-piperidinocarbonyl-Phe-Sta-Ile AMPA
4-BOC-amino-piperidinocarbonyl-Phe-AHPP-Ile AMPA
4-Dimethylamino-piperidinocarbonyl-Phe-Gly-AHCP-Ile AMPA, m.p. 124°-125°
4-Dimethylamino-piperidinocarbonyl-Phe-Gly-AHCP-Ile ADPA
4-Dimethylamino-piperidinocarbonyl-Phe-βAla-AHCP-Ile AMPA dihydrochloride, m.p. 261° (dec.)
4-Dimethylamino-piperidinocarbonyl-Phe-βAla-AHCP-Ile ADPA
4-Ethoxycarbonyl-piperidinocarbonyl-Phe-Gly-AHCP-Ile AMPA
4-Ethoxycarbonyl-piperidinocarbonyl-Phe-Gly-AHCP-Ile ADPA
4-Ethoxycarbonyl-piperidinocarbonyl-Phe-βAla-AHCP-Ile AMPA, m.p. 132°-133°
4-Ethoxycarbonyl-piperidinocarbonyl-Phe-βAla-AHCP-Ile ADPA
N-(Ethoxycarbonylmethyl)-carbamoyl-Phe-Gly-AHCP-Ile AMPA
N-(Ethoxycarbonylmethyl)-carbamoyl-Phe-Gly-AHCP-Ile ADPA
N-(Ethoxycarbonylmethyl)-carbamoyl-Phe-βAla-AHCP-Ile AMPA
N-(Ethoxycarbonylmethyl)-carbamoyl-Phe-βAla-AHCP-Ile ADPA
N-(4-Methoxycarbonylbutyl)-carbamoyl-Phe-Gly-AHCP-Ile AMPA
N-(4-Methoxycarbonylbutyl)-carbamoyl-Phe-Gly-AHCP-Ile ADPA
N-(4-Methoxycarbonylbutyl)-carbamoyl-Phe-βAla-AHCP-Ile AMPA
N-(4-Methoxycarbonylbutyl)-carbamoyl-Phe-βAla-AHCP-Ile ADPA
N-(6-Methoxycarbonylhexyl)-carbamoyl-Phe-Gly-AHCP-Ile AMPA
N-(6-Methoxycarbonylhexyl)-carbamoyl-Phe-Gly-AHCP-Ile ADPA
N-(6-Methoxycarbonylhexyl)-carbamoyl-Phe-βAla-AHCP-Ile AMPA
N-(6-Methoxycarbonylhexyl)-carbamoyl-Phe-βAla-AHCP-Ile ADPA.

Example 6

6-Methoxycarbonyl-hexanoyl-Phe-Gly-AHCP-Ile ADPA, m.p. 176°-177°, is obtained in analogy to Example 4 by condensation of 6-methoxycarbonyl-hexanoyl-Phe-Gly-OH with H-AHCP-Ile ADPA.

The following are obtained analogously
3-Methoxycarbonyl-propionyl-Phe-Gly-AHCP-Ile AMPA
3-Methoxycarbonyl-propionyl-Phe-Gly-AHCP-Ile ADPA
3-Methoxycarbonyl-propionyl-Phe-βAla-AHCP-Ile AMPA 3-Methoxycarbonyl-propionyl-Phe-βAla-AHCP-Ile ADPA
4-Ethoxycarbonyl-butyryl-Phe-Gly-AHCP-Ile AMPA
4-Ethoxycarbonyl-butyryl-Phe-Gly-AHCP-Ile ADPA
4-Ethoxycarbonyl-butyryl-Phe-βAla-AHCP-Ile AMPA
4-Ethoxycarbonyl-butyryl-Phe-βAla-AHCP-Ile ADPA
5-Ethoxycarbonyl-pentanoyl-Phe-Gly-AHCP-Ile AMPA
5-Ethoxycarbonyl-pentanoyl-Phe-Gly-AHCP-Ile ADPA
5-Ethoxycarbonyl-pentanoyl-Phe-βAla-AHCP-Ile AMPA
5-Ethoxycarbonyl-pentanoyl-Phe-βAla-AHCP-Ile ADPA
6-Methoxycarbonyl-hexanoyl-Phe-Gly-AHCP-Ile AMPA, m.p. 88°–89°
6-Methoxycarbonyl-hexanoyl-Phe-Gly-AHCP-Leu AMPA
6-Methoxycarbonyl-hexanoyl-Phe-Gly-AHCP-Leu ADPA
6-Methoxycarbonyl-hexanoyl-Phe-βAla-AHCP-Ile AMPA
6-Methoxycarbonyl-hexanoyl-Phe-βAla-AHCP-Ile ADPA
6-Methoxycarbonyl-hexanoyl-Phe-βAla-AHCP-Leu AMPA
6-Methoxycarbonyl-hexanoyl-Phe-βAla-Leu ADPA
4-CBZ-amino-butyryl-Phe-Gly-AHCP-Ile AMPA
4-CBZ-amino-butyryl-Phe-Gly-AHCP-Ile ADPA
4-CBZ-amino-butyryl-Phe-βAla-AHCP-Ile AMPA, m.p. 210°–211°
4-CBZ-amino-butyryl-Phe-βAla-AHCP-Ile ADPA
5-CBZ-amino-pentanoyl-Phe-Gly-AHCP-Ile AMPA
5-CBZ-amino-pentanoyl-Phe-Gly-AHCP-Ile ADPA
5-CBZ-amino-pentanoyl-Phe-βAla-AHCP-Ile AMPA
5-CBZ-amino-pentanoyl-Phe-βAla-AHCP-Ile ADPA
6-CBZ-amino-hexanoyl-Mal-Gly-AHCP-Ile AMPA, m.p. 179°–180°
6-CBZ-amino-hexanoyl-Mal-Gly-AHCP-Ile ADPA, m.p. 186°–187°
6-CBZ-amino-hexanoyl-Mal-βAla-AHCP-Ile AMPA, m.p. 208°–209°
6-CBZ-amino-hexanoyl-Mal-βAla-AHCP-Ile ADPA, m.p. 244° (decomposition)
6-N'-Cyanoguanidino-hexanoyl-Phe-Gly-AHCP-Ile AMPA
6-N'-Cyanoguanidino-hexanoyl-Phe-Gly-AHCP-Ile ADPA
6-N'-Cyanoguanidino-hexanoyl-Phe-βAla-AHCP-Ile AMPA
6-N'-Cyanoguanidino-hexanoyl-Phe-βAla-AHCP-Ile ADPA
3-Benzyloxysulfonyl-propionyl-Phe-Gly-AHCP-Ile AMPA
3-Benzyloxysulfonyl-propionyl-Phe-Gly-AHCP-Ile ADPA
3-Benzyloxysulfonyl-propionyl-Phe-βAla-AHCP-Ile AMPA
3-Benzyloxysulfonyl-propionyl-Phe-βAla-AHCP-Ile ADPA
2S-Isopropyl-4S-hydroxy-5S-(BOC-amino-piperidinocarbonyl-Phe-Gly-amino)-7-methyl-octanoyl-Ile AMPA
2S-Isopropyl-4S-hydroxy-5S-(BOC-amino-piperidinocarbonyl-Phe-Gly-amino)-7-methyl-octanoyl-Ile ADPA
2S-Isopropyl-4S-hydroxy-5S-(BOC-amino-piperidinocarbonyl-Phe-βAla-amino)-7-methyl-octanoyl-Ile AMPA, m.p. 199°–200°
2S-Isopropyl-4S-hydroxy-5S-(BOC-amino-piperidinocarbonyl-Phe-βAla-amino)-7-methyl-octanoyl-Ile ADPA.

Example 7

8-BOC-amino-octanoyl-Phe-Gly-AHCP-Ile p-sulfamoylanilide, m.p. 154°–157°, is obtained in analogy to Example 4 by condensation of 8-BOC-amino-octanoyl-Phe-Gly-AHCP-OH with H-Ile p-sulfamoylanilide.

The following are obtained analogously

4-BOC-amino-butyryl-Phe-Gly-AHCP-Ile p-sulfamoylanilide
4-BOC-amino-butyryl-Phe-Gly-AHCP-Leu p-sulfamoylanilide
4-BOC-amino-butyryl-Phe-βAla-AHCP-Ile p-sulfamoylanilide
4-BOC-amino-butyryl-Phe-βAla-AHCP-Leu p-sulfamoylanilide
5-BOC-amino-pentanoyl-Phe-Gly-AHCP-Ile p-sulfamoylanilide
5-BOC-amino-pentanoyl-Phe-Gly-AHCP-Leu p-sulfamoylanilide
5-BOC-amino-pentanoyl-Phe-βAla-AHCP-Ile p-sulfamoylanilide
5-BOC-amino-pentanoyl-Phe-βAla-AHCP-Leu p-sulfamoylanilide
6-BOC-amino-hexanoyl-Phe-Gly-AHCP-Ile p-sulfamoylanilide, m.p. 158°–161°
6-BOC-amino-hexanoyl-Phe-Gly-AHCP-Leu p-sulfamoylanilide
6-BOC-amino-hexanoyl-Phe-βAla-AHCP-Ile p-sulfamoylanilide
6-BOC-amino-hexanoyl-Phe-βAla-AHCP-Leu p-sulfamoylanilide
7-BOC-amino-heptanoyl-Phe-Gly-AHCP-Ile p-sulfamoylanilide
7-BOC-amino-heptanoyl-Phe-Gly-AHCP-Leu p-sulfamoylanilide
7-BOC-amino-heptanoyl-Phe-βAla-AHCP-Ile-p-sulfamoylanilide
7-BOC-amino-heptanoyl-Phe-βAla-AHCP-Leu p-sulfamoylanilide
8-BOC-amino-octanoyl-Phe-Gly-AHCP-Leu p-sulfamoylanilide
8-BOC-amino-octanoyl-Phe-βAla-AHCP-Ile p-sulfamoylanilide
8-BOC-amino-octanoyl-Phe-βAla-AHCP-Leu p-sulfamoylanilide
4-Dimethylamino-butyryl-Phe-Gly-AHCP-Abu AMPA
4-Dimethylamino-butyryl-Phe-Gly-AHCP-Ala AMPA
4-Dimethylamino-butyryl-Phe-Gly-AHCP-Cal AMPA
4-Dimethylamino-butyryl-Phe-Gly-AHCP-Met AMPA
4-Dimethylamino-butyryl-Phe-Gly-AHCP-Nle AMPA
4-Dimethylamino-butyryl-Phe-Gly-AHCP-Nva AMPA
4-Dimethylamino-butyryl-Phe-Gly-AHCP-Phe AMPA
4-Dimethylamino-butyryl-Phe-Gly-AHCP-Trp AMPA
4-Dimethylamino-butyryl-Phe-Gly-AHCP-Tyr AMPA
4-Dimethylamino-butyryl-Phe-Gly-AHCP-Val AMPA.

Example 8

6-BOC-amino-hexanoyl-Phe-Gly-AHCP-Ile-Ala AMPA is obtained in analogy to Example 4 from 6-BOC-aminohexanoyl-Phe-Gly-AHCP-Ile-OH and H-Ala AMPA.

Example 9

6-CBZ-amino-hexanoyl-Phe-$\beta$Ala-AHCP-Ile AMPA, m.p. 200°–201°, is obtained in analogy to Example 4 from 6-CBZ-amino-hexanoyl-Phe-$\beta$Ala-AHCP-Ile-OH and 4-amino-5-aminomethyl-2-methylpyrimidine.

The following are obtained analogously:
4-Methyl-piperidino-carbonyl-Phe-$\beta$Ala-AHCP-Ile AMPA
4-Hydroxy-piperidino-carbonyl-Phe-$\beta$Ala-AHCP-Ile AMPA, hydrochloride, m.p. 176° (dec.)
4-Methylamino-piperidino-carbonyl-Phe-$\beta$Ala-AHCP-Ile AMPA
4-Acetamido-piperidino-carbonyl-Phe-$\beta$Ala-AHCP-Ile AMPA, m.p. 183°–187°
4-POA-amino-piperidino-carbonyl-Phe-$\beta$Ala-AHCP-Ile AMPA
4-(2-Hydroxyethyl)-piperazino-carbonyl-Phe-$\beta$Ala-AHCP-Ile AMPA
4-Carbamoyl-piperidino-carbonyl-Phe-$\beta$Ala-AHCP-Ile AMPA
4-(2-Trimethylammonia-ethyl)-piperazino-carbonyl-Phe-$\beta$Ala-AHCP-Ile AMPA chloride.

Example 10

A solution of 1.56 g of 5-dimethylaminopentyl isocyanate in 16 ml of THF is added dropwise at 20° to a stirred solution of 6.52 g of H-Phe-Gly-AHCP-Ile AMPA in 65 ml of THF. The mixture is stirred at 20° for 3 hours, and the usual working out results in N-(5-dimethylaminopentyl)-carbamoyl-Phe-Gly-AHCP-Ile AMPA.

The following are obtained analogously with the corresponding isocyanates:
N-(2-Dimethylaminoethyl)-carbamoyl-Phe-Gly-AHCP-Ile AMPA
N-(2-Dimethylaminoethyl)-carbamoyl-Phe-$\beta$Ala-AHCP-Ile AMPA
N-(3-Dimethylaminopropyl)-carbamoyl-Phe-Gly-AHCP-Ile AMPA
N-(3-Dimethylaminopropyl)-carbamoyl-Phe-$\beta$Ala-AHCP-Ile AMPA
N-(5-Dimethylaminopentyl)-carbamoyl-Phe-$\beta$Ala-AHCP-Ile AMPA, m.p. 184–185
N-(5-Dimethylaminopentyl)-carbamoyl-Mal-Gly-AHCP-Ile AMPA
N-(5-Dimethylaminopentyl)-carbarmoyl-Mal-$\beta$Ala-AHCP-Ile AMPA
3-[(N-(5-Dimethylaminopentyl)-carbamoyl-Phe]-propionyl-AHCP-Ile AMPA
4-[N-(5-Dimethylaminopentyl)-carbamoyl-Phe]-3-thiabutyryl-AHCP-Ile AMPA.

Example 11

A solution of 1 g of 4-BOC-amino-piperidinocarbonyl-Phe-$\beta$Ala-AHCP-Ile AMPA [obtainable by reaction of 80C-AHCP-Ile AMPA (m.p. 218°–220°) with HCL/dioxane to give H-AHCP-Ile AMPA and reaction with 4-BOC-amino-piperidinocarbonyl-Phe-$\beta$Ala-OH] in 20 ml 6f 4N HCL in dioxane is stirred at 20° for 30 min and then evaporated. 4-Amino-piperidinocarbonyl-Phe-$\beta$Ala-AHCP-Ile AMPA dihydrochloride, m.p. 229° (decomposition), is obtained. 2/3 citrate, m.p. 172°

The following are obtained analogously from the corresponding BOC derivatives:
H-$\beta$Ala-Phe-Gly-AHCP-Ile AMPA
H-$\beta$Ala-Phe-Gly-AHCP-Ile ADPA
H-$\beta$Ala-Phe-Gly-AHCP-Leu AMPA
H-$\beta$Ala-Phe-Gly-AHCP-Leu ADPA
H-$\beta$Ala-Phe-$\beta$Ala-AHCP-Ile AMPA
H-$\beta$Ala-Phe-$\beta$Ala-AHCP-Ile ADPA
H-$\beta$Ala-Phe-$\beta$Ala-AHCP-Leu AMPA
H-$\beta$Ala-Phe-$\beta$Ala-AHCP-Leu ADPA
4-Aminobutyryl-Phe-Gly-AHCP-Ile AMPA, dihydrochloride, m.p. 215° (decomposition)
4-Aminobutyryl-Phe-Gly-AHCP-Ile ADPA
4-Aminobutyryl-Phe-Gly-AHCP-Leu AMPA
4-Aminobutyryl-Phe-Gly-AHCP-Leu ADPA
4-Aminobutyryl-Phe-$\beta$Ala-AHCP-Ile AMPA, dihydrochloride, m.p. 199° (decomposition)
4-Aminobutyryl-Phe-$\beta$Ala-AHCP-Ile ADPA
4-Aminobutyryl-Phe-$\beta$Ala-AHCP-Leu AMPA
4-Aminobutyryl-Phe-$\beta$Ala-AHCP-Leu ADPA
4-Aminobutyryl-Mal-Gly-AHCP-Ile AMPA
4-Aminobutyryl-Mal-Gly-AHCP-Ile ADPA
4-Aminobutyryl-Mal-$\beta$Ala-AHCP-Ile AMPA
4-Aminobutyryl-Mal-$\beta$Ala-AHCP-Ile ADPA
5-Aminopentanoyl-Phe-Gly-AHCP-Ile AMPA
5-Aminopentanoyl-Phe-Gly-AHCP-Ile ADPA
5-Aminopentanoyl-Phe-$\beta$Ala-AHCP-Ile AMPA
5-Aminopentanoyl-Phe-$\beta$Ala-AHCP-Ile ADPA
6-Aminohexanoyl-Phe-Gly-AHCP-Ile amide
6-Aminohexanoyl-Phe-$\beta$Ala-AHCP-Ile amide
6-Aminohexanoyl-Phe-Gly-AHCP-Ile AMPA, dihydrochloride, m.p. 180° (decomposition)
6-Aminohexanoyl-Phe-Gly-AHCP-Ile ADPA, m.p. 193°–194°; dihydrochloride, m.p. 106°–107°
6-Aminohexanoyl-Phe-Gly-AHCP-Leu AMPA
6-Aminohexanoyl-Phe-Gly-AHCP-Leu ADPA
6-Aminohexanoyl-Phe-$\beta$Ala-AHCP-Ile AMPA, m.p. 203° (decomposition); dihydrochloride, m.p. 206° (decomposition)
6-Aminohexanoyl-Phe-$\beta$Ala-AHCP-Ile ADPA
6-Aminohexanoyl-Phe-$\beta$Ala-AHCP-Leu AMPA
6-Aminohexanoyl-Phe-$\beta$Ala-AHCP-Leu ADPA
6-Aminohexanoyl-Mal-Gly-AHCP-Ile AMPA, dihydrochloride, m.p. 201°–202°
6-Aminohexanoyl-Mal-Gly-AHCP-Ile ADPA, dihydrochloride, m.p. 197°–198°
6-Aminohexanoyl-Mal-$\beta$Ala-AHCP-Ile AMPA, dihydrochloride, m.p. 192°–193°
6-Aminohexanoyl-Mal-$\beta$Ala-AHCP-Ile ADPA
6-Aminohexanoyl-Phe-Gly-AHCP-Ile N-3-pyridylmethylamide, dihydrochloride, m.p. 104° (dec.)
6-Aminohexanoyl-Phe-$\beta$Ala-AHCP-Ile N-3-pyridylmethylamide
6-Aminohexanoyl-Phe-Gly-AHCP-Ile N-m-aminomethyl-benzylamide
6-Aminohexanoyl-Phe-$\beta$Ala-AHCP-Ile N-m-aminomethyl-benzylamide
6-Aminohexanoyl-Phe-Gly-AHCP-Ile N-p-dimethylaminomethyl-benzylamide
6-Aminohexanoyl-Phe-$\beta$Ala-AHCP-Ile N-p-dimethylaminomethyl-benzylamide
6-Aminohexanoyl-Phe-Gly-AHCP-Ile N-5-tetrazolylmethylamide
6-Aminohexanoyl-Phe-$\beta$Ala-AHCP-Ile N-5-tetrazolylmethylamide 6-Aminohexanoyl-Phe-Gly-AHCP-Ile N-3-dimethylaminopropylamide
6-Aminohexanoyl-Phe-βAla-Ile N-3-dimethylaminopropylamide
6-Aminohexanoyl-Phe-Gly-AHCP-Ile N-2-sulfoethylamide
6-Aminohexanoyl-Phe-βAla-AHCP-Ile N-2-sulfoethylamide
3-[6-Aminohexanoyl-Phe]-propionyl-AHCP-Ile AMPA
3-[6-Aminohexanoyl-Phe]-propionyl-AHCP-Ile ADPA
4-[6-Aminohexanoyl-Phe]-3-thiabutyryl-AHCP-Ile AMPA
4-[6-Aminohexanoyl-Phe]-3-thiabutyryl-AHCP-Ile ADPA
7-Aminoheptanoyl-Phe-Gly-AHCP-Ile AMPA
7-Aminoheptanoyl-Phe-Gly-AHCP-Ile ADPA
7-Aminoheptanoyl-Phe-βAla-AHCP-Ile AMPA
7-Aminoheptanoyl-Phe-βAla-AHCP-Ile ADPA
8-Aminooctanoyl-Phe-Gly-AHCP-Ile-AMPA, dihydrochloride, m.p. 165° (dec.)
8-Aminooctanoyl-Phe-Gly-AHCP-Ile ADPA
8-Aminooctanoyl-Phe-βAla-AHCP-Ile AMPA, dihydrochloride, m.p. 165° (dec.)
8-Aminooctanoyl-Phe-βAla-AHCP-Ile ADPA
4-Amino-piperidinocarbonyl-Phe-Gly-AHCP-Ile AMPA, dihydrochloride, m.p. 160°-161°
4-Amino-piperidinocarbonyl-Phe-Gly-AHCP-Ile ADPA
4-Amino-piperidinocarbonyl-Phe-Gly-AHCP-Leu AMPA
4-Amino-piperdinocarbonyl-Phe-Gly-AHCP-Leu ADPA
4-Amino-piperidinocarbonyl-Phe-βAla-AHCP-Ile AMPA
4-Amino-piperidinocarbonyl-Phe-βAla-AHCP-Ile ADPA, dihydrochloride, m.p. 159°-160°
4-Amino-piperidinocarbonyl-Phe-βAla-AHCP-Ile N-2-pyridylmethylamide
4-Amino-piperidinocarbonyl-Phe-βAla-AHCP-Ile N-3-pyridylmethylamide, dihydrochloride, m.p. 176°-177°
4-Amino-piperidinocarbonyl-Phe-βAla-AHCP-Leu AMPA, dihydrochloride, m.p. 280° (dec.)
4-Amino-piperidinocarbonyl-Phe-βAla-AHCP-Leu ADPA
4-Amino-piperidinocarbonyl-Phe-Gly-AHCH-Ile AMPA
4-Amino-piperidinocarbonyl-Phe-Sta-Ile AMPA
4-Amino-piperidinocarbonyl-Phe-AHPP-Ile AMPA
2S-Isopropyl-4S-hydroxy-5S-(4-amino-piperidinocarbonyl-Phe-Gly-amino)-7-methyl-octanoyl-Ile AMPA
2S-Isopropyl-4S-hydroxy-5S-(4-amino-piperidinocarbonyl-Phe-Gly-amino)-7-methyl-octanoyl-Ile ADPA
2S-Isopropyl-4S-hydroxy-5S-(4-amino-piperidinocarbonyl-Phe-βAla-amino)-7-methyl-octanoyl-Ile AMPA, dihydrochloride, m.p. 182°-183°
2S-Isopropyl-4S-hydroxy-5S-(4-amino-piperidinocarbonyl-Phe-βAla-amino)-7methyl-octanoyl-Ile ADPA
4-Amino-butyryl-Phe-Gly-AHCP-Ile p-sulfamoylanilide
4-Amino-butyryl-Phe-Gly-AHCP-Leu p-sulfamoylanilide
4-Amino-butyryl-Phe-βAla-AHCP-Ile p-sulfamoylanilide
4-Amino-butyryl-Phe-βAla-AHCP-Leu p-sulfamoylanilide
5-Amino-pentanoyl-Phe-Gly-AHCP-Ile p-sulfamoylanilide
5-Amino-pentanoyl-Phe-Gly-AHCP-Leu p-sulfamoylanilide
5-Amino-pentanoyl-Phe-βAla-AHCP-Ile p-sulfamoylanilide
5-Amino-pentanoyl-Phe-βAla-AHCP-Leu p-sulfamoylanilide
6-Amino-hexanoyl-Phe-Gly-AHCP-Ile p-sulfamoylanilide, dihydrochloride, m.p. 98°
6-Amino-hexanoyl-Phe-Gly-AHCP-Leu p-sulfamoylanilide
6-Amino-hexanoyl-Phe-βAla-AHCP-Ile p-sulfamoylanilide
6-Amino-hexanoyl-Phe-βAla-AHCP-Leu p-sulfamoylanilide
7-Amino-heptanoyl-Phe-Gly-AHCP-Ile p-sulfamoylanilide
7-Amino-heptanoyl-Phe-Gly-AHCP-Leu p-sulfamoylanilide
7-Amino-heptanoyl-Phe-βAla-AHCP-Ile p-sulfamoylanilide
7-Amino-heptanoyl-Phe-βAla-AHCP-Leu p-sulfamoylanilide
8-Amino-octanoyl-Phe-Gly-AHCP-Ile p-sulfamoylanilide, dihydrochloride, m.p. 102°
8-Amino-octanoyl-Phe-Gly-AHCP-Ile p-sulfamoylanilide
8-Amino-octanoyl-Phe-βAla-AHCP-Ile p-sulfamoylanilide
8-Amino-octanoyl-Phe-βAla-AHCP-Leu p-sulfamoylanilide.

Example 12

A mixture of 1 g of 6-methoxycarbonyl-hexanoyl-Phe-Gly-AHCP-Ile ADPA, 50 ml of dioxane and 20 ml of 2N NaOh (aqueous) is stirred at 20° for 3 hours. The usual working up results in 6-carboxy-hexanoyl-Phe-Gly-AHCP-Ile ADPA, m.p. 170°-171°.

The following are obtained analogously by hydrolysis:

3-Carboxy-propionyl-Phe-Gly-AHCP-Ile AMPA
3-Carboxy-propionyl-Phe-Gly-AHCP-Ile ADPA
3-Carboxy-propionyl-Phe-βAla-AHCP-Ile AMPA
3-Carboxy-propionyl-Phe-βAla-AHCP-Ile ADPA
4-Carboxy-butyryl-Phe-Gly-AHCP-Ile AMPA
4-Carboxy-butyryl-Phe-Gly-AHCP-Ile ADPA
4-Carboxy-butyryl-Phe-βAla-AHCP-Ile AMPA
4-Carboxy-butyryl-Phe-βAla-AHCP-Ile ADPA
5-Carboxy-pentanoyl-Phe-Gly-AHCP-Ile AMPA
5-Carboxy-pentanoyl-Phe-Gly-AHCP-Ile ADPA
5-Carboxy-pentanoyl-Phe-βAla-AHCP-Ile AMPA
51-Carboxy-pentanoyl-Phe-βAla-AHCP-Ile ADPA
6-Carboxy-hexanoyl-Phe-Gly-AHCP-Ile AMPA, m.p. 185°-186° (decomposition); hydrochoride, m.p. 162° (decomposition)
6-Carboxy-hexanoyl-Phe-Gly-AHCP-Leu AMPA
6-Carboxy-hexanoyl-Phe-Gly-AHCP-Leu ADPA
6-Carboxy-hexanoyl-Phe-⊕Ala-AHCP-Ile AMPA
6-Carboxy-hexanoyl-Phe-βAla-AHCP-Ile ADPA
6-Carboxy-hexanoyl-Phe-βAla-AHCP-Leu AMPA
6-Carboxy-hexanoyl-Phe-βAla-AHCP-Leu ADPA
4-Carboxy-piperidinocarbonyl-Phe-Gly-AHCP-Ile AMPA
4-Carboxy-piperidinocarbonyl-Phe-Gly-AHCP-Ile ADPA
4-Carboxy-piperidinocarbonyl-Phe-βAla-AHCP-Ile AMPA, hydrochloride, m.p. 212°(dec.)

4-Carboxy-piperidinocarbonyl-Phe-βAla-AHCP-Ile ADPA
N-(Carboxymethyl)-carbamoyl-Phe-Gly-AHCP-Ile AMPA
N-(Carboxymethyl)-carbamoyl-Phe-Gly-AHCP-Ile ADPA
N-(Carboxymethyl)-carbamoyl-Phe-βAla-AHCP-Ile AMPA
N-(Carboxymethyl)-carbamoyl-Phe-βAla-AHCP-Ile ADPA
N-(4-Carboxybutyl)-carbamoyl-Phe-Gly-AHCP-Ile AMPA
N-(4-Carboxybutyl)-carbamoyl-Phe-Gly-AHCP-Ile ADPA
N-(4-Carboxybutyl)-carbamoyl-Phe-βAla-AHCP-Ile AMPA
N-(4-Carboxybutyl)-carbamoyl-Phe-βAla-AHCP-Ile ADPA
N-(6-Carboxyhexyl)-carbamoyl-Phe-Gly-AHCP-Ile AMPA
N-(6-Carboxyhexyl)-carbamoyl-Phe-Gly-AHCP-Ile ADPA
N-(6-Carboxyhexyl)-carbamoyl-Phe-βAla-AHCP-Ile AMPA
N-(6-Carboxyhexyl)-carbamoyl-Phe-βAla-AHCP-Ile ADPA.

EXAMPLE 13

6-Amino-hexanoyl-Phe-βAla-AHCP-Ile AMPA, m.p. 203° (decomposition), is obtained in analogy to Example 2 from 6-CBZ-amino-hexanoyl-Phe-βAla-AHCP-Ile AMPA by hydrogenolysis.

The following are obtained analogously by hydrogenolysis of the corresponding CBZ derivatives:
2-Amino-2-methyl-propionyl-Phe-Gly-AHCP-Ile AMPA
2-Amino-2-methyl-propionyl-Phe-Gly-AHCP-Ile ADPA
2-Amino-2-methyl-propionyl-Phe-βAla-AHCP-Ile AMPA dihydrochloride, m.p. 212°
2-Amino-2-methyl-propionyl-Phe-βAla-AHCP-Ile ADPA
2-Amino-2-methyl-propionyl-Mal-Gly-AHCP-Ile AMPA dihydrochloride, m.p. 118° (dec.)
2-Amino-2-methyl-propionyl-Mal-Gly-AHCP-Ile ADPA
2-Amino-2-methyl-propionyl-Mal-βAla-AHCP-Ile AMPA
2-Amino-2-methyl-propionyl-Mal-βAla-AHCP-Ile ADPA.

EXAMPLE 14

3-Sulpho-propionyl-Phe-Gly-AHCP-Ile AMPA is obtained in analogy to Example 2 from 3-benzyloxysulfonyl-propionyl-Phe-Gly-AHCP-Ile AMPA by hydrogenolysis.

The following are obtained analogously by hydrogenolysis of the corresponding benzyl esters:
3-Sulfo-propionyl-Phe-Gly-AHCP-Ile ADPA
3-Sulfo-propionyl-Phe-βAla-AHCP-Ile AMPA
3-Sulfo-propionyl-Phe-βAla-AHCP-Ile ADPA.

EXAMPLE 15 a) 3-Oxo-4S-(4-dimethylaminobutyryl-Phe-Gly-amino)-5-cyclohexyl-pentanoyl-Ile AMPA is obtained in analogy to Example 4 from 4-dimethylaminobutyryl-Phe-Gly-OH and 3-oxo-4S-amino-5-cyclohexyl-pentanoyl-Ile AMPA.

b) A solution of 1 g of the abovementioned keto amide in 25 ml of CH$_3$OH is hydrogenated on 0.1 g of 10% Pd-C at 20° and under 1 bar until H$_2$ uptake ceases. Filtration and evaporation result in a mixture of 3R- and 3S-hydroxy-4S-(4-dimethylaminobutyryl-Phe-Gly-amino)-5-cyclohexyl-pentanoyl-Ile AMPA.

EXAMPLE 16

70 mg of hydroxylamine hydrochloride are added to a solution of 763 mg of 3-oxo-4S-(4-dimethylaminobutyryl-Phe-Gly-amino)-5-cyclohexylpentanoyl-Ile AMPA and 1.43 g of Na$_2$CO$_3$.10 H$_2$O in 5 ml of methanol and 5 ml of water, and the mixture is stirred at 20° for 14 hours. The precipitated oxime is filtered off, dried, dissolved in 10 ml of methanol and hydrogenated on 0.5 g of Raney Ni at 20° and under 5 bar. The catalyst is filtered off, the filtrate is evaporated, the resulting mixture is separated on silica gel, and 3S-amino-4S-(4-dimethylaminobutyryl-Phe-Gly-amino)-5-cyclohexylpentanoyl-Ile AMPA ("4-dimethylaminobutyryl-Phe-Gly-DACP-Ile AMPA") is obtained; the 3R-amino epimer is also obtained.

EXAMPLE 17

Analogously to Example 4, the following are obtained:
1-Methyl-4-piperidinyl-carbonyl-Phe-βAla-AHCP-Ile-AMPA, m.p. 187°–189°
4-BOC-amino-piperidinocarbonyl-Phe-βAla-Sta-Ile-AMPA, m.p. 151°–152°
6-BOC-amino-hexanoyl-N-methyl-Mal-Gly-AHCP-Ile-AMPA, m.p. 100° (dec.)
4-BOC-amino-piperidinocarbonyl-Phe-βAla-AHCP-Gly-AMPA, m.p. 181° (dec.)
3-(1-Methyl-2-piperidyl)-propionyl-Phe-βAla-AHCP-Ile-AMPA, m.p. 202°
3-(1-Methyl-2-piperidyl)-propionyl-Phe-Gly-AHCP-Ile-AMPA, oil
4-(1-Methyl-2-piperidyl)-butyryl-Phe-Gly-AHCP-Ile-AMPA, diacetate, oil
4-(1-Methyl-2-piperidyl)-butyryl-Phe-βAla-AHCP-Ile-AMPA, diacetate, m.p. 206°
4-BOC-amino-piperidinocarbonyl-Phe-βAla-AHCP-Ala-AMPA, m.p. 181°–182°
Pyrrolidinocarbonyl-Phe-βAla-AHCP-Ile-AMPA, hydrochloride, m.p. 136°–137°
Morpholinocarbonyl-Phe-βAla-AHCP-Ile-AMPA, hydrochloride, m.p. 157°–158°
4-BOC-amino-piperidinocarbonyl-Mal-Gly-AHCP-Ile-AMPA, m.p. 193°–194°
Piperidinocarbonyl-Phe-βAla-AHCP-Ile-AMPA, hydrochloride, m.p. 140°–141°
4-BOC-amino-piperidinoacetyl-Phe-Gly-AHCP-Ile-AMPA, m.p. 135°
4-BOC-amino-piperidinocarbonyl-Phe-βAla-AHCP-Nle-AMPA, m.p. 145°–146°
3-BOC-amino-3-methyl-butyryl-Phe-Gly-AHCP-Ile-AMPA, m.p. 102° (dec.)
4-BOC-amino-piperidinocarbonyl-Leu-βAla-AHCP-Ile-AMPA, m.p. 183° (dec.)
3-BOC-amino-3-methyl-butyryl-Phe-Gly-AHCP-Ile-(N-3-pyridylmethyl-amide), m.p. 90° (dec.)
4-Methylsulfonamido-piperidinocarbonyl-Phe-βAla-AHCP-Ile-AMPA, hydrochloride, m.p. 159°–160°
4-(3-Hydroxypropyl)-piperazinocarbonyl-Phe-βAla-AHCP-Ile-AMPA, dihydrochloride, m.p. 182° (dec.)

4-BOC-piperazinocarbonyl-Phe-βAla-AHCP-Ile-AMPA, m.p. 140°–141°

Benzyl 4-BOC-amino-piperidinocarbonyl-Phe-βAla-AHCP-Ile-amino-acetate

Benzyl 3-(4-BOC-amino-piperidinocarbonyl-Phe-βAla-AHCP-Ile-amino)-propionate

Benzyl 4-(4-BOC-amino-piperidinocarbonyl-Phe-βAla-AHCP-Ile-amino)-butyrate

Benzyl 5-(4-BOC-amino-piperidinocarbonyl-Phe-βAla-AHCP-Ile-amino)-pentanoate, m.p. 102°–103°

Benzyl 6-(4-BOC-amino-piperidinocarbonyl-Phe-βAla-AHCP-Ile-amino)-hexanoate, m.p. 110°–111°

4-Formamido-piperidinocarbonyl-Phe-βAla-AHCP-Ile-AMPA

4-Trifluoroacetamido-piperidinocarbonyl-Phe-βAla-AHCP-Ile-AMPA

4-BOC-amino-piperidinocarbonyl-Phe-βAla-AHCP-D-Ile-AMPA, m.p. 164°–165°

4-BOC-amino-piperidinocarbonyl-Mal-βAla-AHCP-Ile-AMPA, m.p. 183°–184°

3-(4-BOC-amino-piperidinocarbonyl-Phe-amino)-3-methyl-butyryl-AHCP-Ile-AMPA, m.p. 136°–137°

4-BOC-amino-piperidinocarbonyl-D-Phe-βAla-AHCP-Ile-AMPA, m.p. 140°–142°

4-BOC-amino-piperidinocarbonyl-Phe-βAla-AHCP-OMe, m.p. 72°–74°

4-BOC-amino-piperidinocarbonyl-Phe-βAla-AHCP-Ile-OMe, m.p. 114°–115°

4-BOC-amino-piperidinoacetyl-Phe-βAla-AHCP-Ile-AMPA, m.p. 78°–81°

4-Cyano-piperidinocarbonyl-Phe-βAla-AHCP-Ile-AMPA

4-Dimethylaminomethyl-piperidinocarbonyl-Phe-βAla-AHCP-Ile-AMPA

4-BOC-aminomethyl-piperidinocarbonyl-Phe-βAla-AHCP-Ile-AMPA 3-(2-Piperidyl)-propionyl-Phe-βAla-AHCP-Ile-AMPA, tris-(trifluoracetate), oil 3-(2-Piperidyl)-propionyl-Phe-Gly-AHCP-Ile-AMPA, triacetate, oil 4-(2-Piperidyl)-butyryl-Phe-βAla-AHCP-Ile-AMPA, triacetate, m.p. 110°

4-(2-Piperidyl)-butyryl-Phe-Gly-AHCP-Ile-AMPA, triacetate, oil.

EXAMPLE 18

Analogously to Example 11, the following are obtained from the corresponding BOC derivatives:

4-Amino-piperidinocarbonyl-Phe-βAla-Sta-Ile-AMPA, dihydrochloride, m.p. 196° (dec.)

4-Amino-piperidinocarbonyl-Phe-βAla-AHCP-Gly-AMPA, dihydrochloride, m.p. 266° (dec.)

4-Amino-piperidinocarbonyl-Phe-βAla-AHCP-Ala-AMPA, dihydrochloride, m.p. 126°–127°

4-Amino-piperidinocarbonyl-Mal-Gly-AHCP-Ile-AMPA, dihydrochloride, m.p. 192° (dec.)

4-Amino-piperidinoacetyl-Phe-Gly-AHCP-Ile-AMPA, trihydrochloride, m.p. 174°

3-Amino-3-methyl-butyryl-Phe-Gly-AHCP-Ile-AMPA, dihydrochloride, m.p. 230°

4-Amino-piperidinocarbonyl-Leu-βAla-AHCP-Ile-AMPA, dihydrochloride, m.p. 269° (dec.)

3-Amino-3-methyl-butyryl-Phe-Gly-AHCP-Ile-(N-3-pyridylmethyl-amide), dihydrochloride, m.p. 100° (dec.)

4-Amino-piperidinocarbonyl-Phe-βAla-AHCP-D-Ile-AMPA, dihydrochloride, m.p. 122° (dec.)

4-Amino-piperidinocarbonyl-Mal-βAla-AHCP-Ile-AMPA, dihydrochloride, m.p. 116° (dec.)

3-(4-Amino-piperidinocarbonyl-Phe-amino)-3-methyl-butyrylAHCP-Ile-AMPA, dihydrochloride, m.p. 138°

4-Amino-piperidinocarbonyl-D-Phe-βAla-AHCP-Ile-AMPA, dihydrochloride, m.p. 178° (dec.)

4-Amino-piperidinocarbonyl-Phe-βAla-AHCP-OH, hydrochloride, m.p. 102°–105°

4-Amino-piperidinocarbonyl-Phe-βAla-AHCP-Ile-OH, hydrochloride, m.p. 119°–120°

Piperazinocarbonyl-Phe-βAla-AHCP-Ile-AMPA, dihydrochloride, m.p. 183° (dec.)

4-Amino-piperidinoacetyl-Phe-βAla-AHCP-Ile-AMPA, trihydrochloride, m.p. 208°–209°

4-Amino-piperidinocarbonyl-Phe-βAla-AHCP-Ile-amino-acetic acid 3-(4-Amino-piperidinocarbonyl-Phe-βAla-AHCP-Ile-amino)propionic acid 4-(4-Amino-piperidinocarbonyl-Phe-βAla-AHCP-Ile-amino)butyric acid 5-(4-Amino-piperidinocarbonyl-Phe-βAla-AHCP-Ile-amino) pentanoic acid, hydrochloride, m.p. 146°–148°

6-(4-Amino-piperidinocarbonyl-Phe-βAla-AHCP-Ile-amino) hexanoic acid, hydrochloride, m.p. 159°–160°

4-Aminomethyl-piperidinocarbonyl-Phe-βAla-AHCP-Ile-AMPA.

Example 19

Analogously to Example 2, the following are obtained by hydrogenolysis of the corresponding benzyl esters:

4-BOC-amino-piperidinocarbonyl-Phe-βAla-AHCP-Ile-amino-acetic acid 3-(4-BOC-amino-piperidinocarbonyl-Phe-βAla-AHCP-Ile-amino)-propionic acid 4-(4-BOC-amino-piperidinocarbonyl-Phe-βAla-AHCP-Ile-amino)-butyric acid 5-(4-BOC-amino-piperidinocarbonyl-Phe-βAla-AHCP-Ile-amino)-pentanoic acid, m.p. 157°

6-(4-BOC-amino-piperidinocarbonyl-Phe-βAla-AHCP-Ile-amino)-hexanoic acid, m.p. 167°–168°

Example 20

Analogously to Example 12, the following are obtained by saponification of the corresponding methyl esters:

4-BOC-amino-piperidinocarbonyl-Phe-βAla-AHCP-OH, m.p. 112°–113°

4-BOC-amino-piperidinocarbonyl-Phe-βAla-AHCP-Ile-OH, m.p. 93°–95°.

Example 21

A mixture of 792 mg of 4-amino-piperidinocarbonyl-Phe-βAla-AHCP-Ile-AMPA, 90 mg of 5-methylisothiourea, 5 ml of ethanol and 5 of water is stirred for 2 hours at 50° C. After working up as usual, 4-guanidinyl-piperidinocarbonyl-Phe-βAla-AHCP-Ile-AMPA is obtained, m.p. 183°.

Example 22

A mixture of 792 mg of 4-amino-piperidinocarbonyl-Phe-βAla-AHCP-Ile-AMPA, 115 mg (=0.132 ml) of trimethylsilyl-isocyanate and 10 ml of THF is stirred for 16 hours at 20° C. Thereafter, the mixture is stirred into water and worked up as usual, yielding 4-ureidopiperidinocarbonyl-Phe-βAla-AHCP-Ile-AMPA, hydrochloride, m.p. 126°–128° (dec.).

The following are obtained with the corresponding alkyl isocyanates:

4-(N'-Ethylureido)-piperidinocarbonyl-Phe-βAla-AHCP-Ile-AMPA, hydrochloride, m.p. 170°–171°, 4-(N'-Isopropylureido)-piperidinocarbonyl-Phe-βAla-AHCP-Ile-AMPA, hydrochloride, m.p. 187° (dec.).

Example 23

In analogy to Example 4, 4-BOC-amino-piperidinocarbonyl-2-Tia-βAla-AHCP-Ile-AMPA is obtained from 4-BOC-amino-piperidinocarbonyl-2-Tia-OH and H-βAla-AHCP-Ile-AMPA; oil.

The following are obtained analogously:
3-BOC-amino-3-methyl-butyryl-Phe-βAla-AHCP-Ile-AMPA, m.p. 200°–201°

4-BOC-amino-piperidinocarbonyl-Phe-βAla-AHCP-Ile-N-(4-hydroxybutyl)-amide, m.p. 176°

4-BOC-amino-piperidinocarbonyl-Phe-βAla-AHCP-Ile-N-(5-hydroxypentyl)-amide, m.p. 168°–169°

4-BOC-amino-piperidinocarbonyl-Phe-βAla-AHCP-Ile-N-hexyl-amide, m.p. 113°–114°

4-BOC-amino-piperidinocarbonyl-Phe-βAla-AHCP-Ile-N-(5-dimethylaminopentyl)-amide, hydrochloride, m.p. 144° (dec.)

4-BOC-amino-piperidinocarbonyl-3-Pya-βAla-AHCP-Ile-AMPA, oil

4-BOC-amino-piperidinocarbonyl-p-fluoro-L-phenylalanyl-βAla-AHCP-Ile-AMPA, oil 5S-(4-BOC-amino-piperidinocarbonyl-Phe-βAla-amino)-6-cyclohexyl-4S-hydroxy-hexanoyl-Ile-AMPA, oil 5S-(4-BOC-amino-piperidinocarbonyl-Leu-βAla-amino)-4S-hydroxy-2-isopropyl-7-methyl-octanoyl-Ile-AMPA, m.p. 219°–220°

5S-(4-BOC-amino-piperidinocarbonyl-Leu-βAla-amino)-4S-hydroxy-7-methyl-octanoyl-Ile-AMPA, m.p. 170°–171°

4-BOC-amino-piperidinocarbonyl-Phe-βAla-AHCP-Ile-N-(1-benzyl-4-piperidinyl)-amide, oil 4-BOC-amino-piperidinocarbonyl-Tyr-βAla-AHCP-Ile-AMPA, oil 4-BOC-amino-piperidinocarbonyl-D-Tyr-βAla-AHCP-Ile-AMPA, oil 4-BOC-amino-piperidinocarbonyl-Phe-βAla-AHCP-Ile-OMe, oil 4-Methylamino-piperidinocarbonyl-Phe-βAla-AHCP-Ile-AMPA, dihydrochloride, m.p. 173°

4-Methyl-piperazinocarbonyl-Phe-βAla-AHCP-Ile-AMPA, dihydrochloride, m.p. 194° (dec.).

Example 24

In analogy to Example 11, 4-Amino-piperidinocarbonyl-2-Tia-βAla-AHCP-Ile-AMPA is obtained from 4-BOC-amino-piperidinocarbonyl-2-Tia-βAla-AHCP-Ile-AMPA with HCl/dioxane; dihydrochloride, m.p. 185°–187°.

The following are obtained analogously:
3-Amino-3-methyl-butyryl-Phe-βAla-AHCP-Ile-AMPA, dihydrochloride, m.p. 231° (dec.)

4-Amino-piperidinocarbonyl-Phe-βAla-AHCP-Ile-N-(4-hydroxybutyl)-amide, hydrochloride, m.p. 155°–156°

4-Amino-piperidinocarbonyl-Phe-βAla-AHCP-Ile-N-(5-hydroxypentyl)-amide, hydrochloride, m.p. 145°–146°

4-Amino-piperidinocarbonyl-Phe-βAla-AHCP-Ile-N-hexyl-amide,hydrochloride, m.p. 169°–170°

4-Amino-piperidinocarbonyl-Phe-βAla-AHCP-Ile-N-(5-dimethylaminopentyl)-amide, dihydrochloride, m.p. 188° (dec.)

4-Amino-piperidinocarbonyl-3-Pya-βAla-AHCP-Ile-AMPA, dihydrochloride, m.p. 125° (dec.)

4-Amino-piperidinocarbonyl-p-fluoro-L-phenylalanyl-βAla-AHCP-Ile-AMPA, dihydrochloride, m.p. 210°–213°

5S-(4-Amino-piperidinocarbonyl-Phe-βAla-amino)-6-cyclohexyl-4S-hydroxy-hexanoyl-Ile-AMPA, dihydrochloride, m.p. 187° (dec.)

5S-(4-Amino-piperidinocarbonyl-Leu-βAla-amino)-4S-hydroxy-2-isopropyl-7-methyl-octanoyl-Ile-AMPA, dihydrochloride, m.p. 103°–105°

4-Amino-piperidinocarbonyl-Phe-βAla-AHCP-Ile-N-(1-benzyl-4-piperidinyl)-amide, dihydrochloride, m.p. 183° (dec.)

4-Amino-piperidinocarbonyl-Tyr-βAla-AHCP-Ile-AMPA, dihydrochloride, m.p. 179°–180°

4-Amino-piperidinocarbonyl-D-Tyr-βAla-AHCP-Ile-AMPA, dihydrochloride. m.p. 158°–159°

4-Amino-piperidinocarbonyl-Phe-βAla-AHCP-Ile-OMe, hydrochloride, m.p. 180° (dec.)

Example 25

In analogy to Example 4, 5S-(4-BOC-amino-piperidinocarbonyl-Phe-βAla-amino)-4S-hydroxy-2S-isopropyl-6-phenyl-hexanoyl-Ile-AMPA is obtained from 4-BOC-amino-piperidinocarbonyl-Phe-βAla-OH and 5S-Amino-4S-hydroxy-2S-isopropyl-6-phenyl-hexanoyl-Ile-AMPA; FAB: 943.

The following are obtained analogously:
5S-(4-BOC-amino-piperidinocarbonyl-Phe-βAla-amino)-4S-hydroxy-2R-isopropyl-6-phenyl-hexanoyl-Ile-AMPA; FAB 943

5S-(4-BOC-amino-piperidinocarbonyl-Phe-βAla-amino)-4S-hydroxy-2S-isopropyl-6-phenyl-hexanoyl-Ile-Val-OMe; FAB: 936

5S-(4-BOC-amino-piperidinocarbonyl-Phe-βAla-amino)-4S-hydroxy-2S-isopropyl-7-methyl-octanoyl-Ile-Val-OMe; FAB: 902

4-BOC-amino-piperidinocarbonyl-Phe-βAla-AHCP-OiPr, m.p. 160°–161°

4-BOC-amino-piperidinocarbonyl-Phe-βAla-AHCP-(N-isobutyl-amide), m.p. 89°–90°

5S-(4-BOC-amino-piperidinocarbonyl-Phe-βAla-amino)-6-cyclohexyl-4S-hydroxy-hexanoyl-(N-butyl-amide), m.p. 99°–100°

4-BOC-amino-piperidinocarbonyl-Phe-βAla-AHPP-Ile-AMPA, m.p. 132°

4-dimethylamino-piperidinocarbonyl-Phe-βAla-AHPP-Ile-AMPA, m.p. 181°–182°

5S-(4-BOC-amino-piperidinocarbonyl-Phe-βAla-amino)-6-cyclohexyl-4S-hydroxy-2R-methyl-hexanoyl-(N-methyl-amide), m.p. 152°–152°

6-Cyclohexyl-4S-hydroxy-5S-(4-hydroxy-piperidinocarbonyl-Phe-βAla-amino)-2R-methyl-hexanoyl-(N-methyl-amide), m.p. 161°–162°

5-[1S-(4-Ethoxycarbonyl-Phe-βAla-AHCP-amino)-2S-methyl-butyl]-tetrazole, m.p. 153°–154°.

Example 26

In analogy to Example 11, 5S-(4-amino-piperidinocarbonyl-Phe-βAla-amino)-4S-hydroxy-2S-isopropyl-7-methyl-octanoyl-Ile-Val-OMe is obtained from 5S-(4-BOC-amino-piperidinocarbonyl-Phe-βAla-amino)-4S-hydroxy-2S-isopropyl-7-methyl-octanoyl-Ile-Val-OMe; hydrochloride, FAB: 802

The following are obtained analogously:

4Amino-piperidinocarbonyl-Phe-βAla-AHCP-(N-isobutyl-amide), TFA, m.p. 142°–144°

5S-(4-Amino-piperidinocarbonyl-Phe-βAla-amino)-6-cyclohexyl-4S-hydroxy-hexanoyl-(N-butyl-amide), TFA, m.p. 136°–137°

4-Amino-piperidinocarbonyl-Phe-βAla-AHPP-Ile-AMPA, m.p. 188°–189°

5S-(4-Amino-piperidinocarbonyl-Phe-βAla-amino)-6-cyclohexyl-4S-hydroxy-2R-methyl-hexanoyl-(N-methyl-amide), TFA, m.p. 138°–140°.

The examples which follow relate to pharmaceutical compositions.

Example A: Tablets

A mixture of 1 kg of 4-aminopiperidinocarbonyl-Phe-βAla-AHCP-Ile AMPA dihydrochloride, 4 kg of lactose, 1.2 kg of maize starch, 200 g of talc and 100 g of magnesium stearate is compressed in a customary manner to give tablets in such a way that each tablet contains 100 mg of active compound.

Example B: Coated tablets

Tablets are compressed in analogy to Example A and are then coated in a customary manner with a coating composed of sucrose, maize starch, talc, tragacanth and colorant.

Example C: Capsules 500 g of 6-amino exanoyl-Phe-Gly-AHCP-Ile AMPA dihydrochloride are dispensed in a customary manner into hard gelatin capsules so that each capsule contains 500 mg of active compound.

Example D: Injection ampoules

A solution of 100 g of the Na salt of 6-carboxyhexanoyl-Phe-Gly-AHCP-Ile ADPA in 4 L of double-distilled water is adjusted to pH 6.5 with 2N hydrochloric acid, filtered sterile and dispensed into injection ampoules. These are lyophilized under sterile conditions and sealed sterile. Each injection ampoule contains 50 mg of active compound.

Example E: Suppositories

A mixture of 50 g of 4-dimethylaminobutyryl-Phe-Gly-AHCP-ILe AMPA dihydrochloride with 10 g of soya lecithin and 140 g of cocoa butter is melted, poured into moulds and left to cool. Each suppository contains 250 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An amino acid compound of formula I

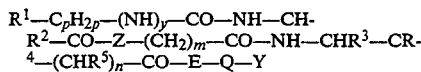

wherein $R^1$ is $R^6R^7N-$, $R^6OOC-$ or $R^6-O-(CH_2CH_2O)_r-$;

$-NH-CHR^2-CO-$ is Leu, Mal, p-F-Phe, Phe, D-Phe, 3-Pya, 2-Tia, Tyr or D-Tyr;

$-Z-C_mH_{2m}-CO-$ is βAla or Gly;

$R^3$ is isobutyl, benzyl or cyclohexylmethyl;

$R^4$ is (H, OH);

$-(CHR^5)_n-$ is $-CH_2-$, $-CH_2CH_2-$, or $-CH_2-CHA-$;

E is absent or is Ala, Gly, Ile, Leu, Nle or Ile-Val;

$Q-Y$ is OH, OA, NHA, $NH-C_tH_{2t}-R^{11}$, $NH-C_tH_{2t}-OH$ or $NH-C_tH_{2t}-NA_2$;

$R^6$ and $R^7$ are each independently H or A;

$R^7$ can also be $R^9-O-CO-$;

$R^9$ is A or benzyl;

$R^6R^7N$ can also be piperidinyl, morpholinyl, piperazinyl or pyrrolidinyl, unsubstituted or substituted by A, OH, $NH_2$, NHA, $NA_2$, $NH-CO-A$, $NH-CO-OA$, $NH-SO_2-A$, hydroxyalkyl, COOH, COOA, $NH-CO-NH_2$, $NH-CO-NHA$ or guanidinyl;

$R^{11}$ is p-aminosulfonylphenyl, 1-benzyl-4-piperidinyl, 3-pyridyl, 4-amino-2-methyl-5-pyrimidinyl, 2-amino-5,6-dimethyl-3-pyrazinyl or 5-tetrazolyl;

y is 0 or 1;

p is 0, 1, 2, 3, 4, 5, 6 or 7;

r is 1 or 2;

t is 1, 2, 3, 4 or 5;

-alkyl- is an alkylene group having 1–8 C atoms; and

A is alkyl having 1–8 C atoms, or a physiologically acceptable salt thereof.

2. A compound according to claim 1, wherein said compound is a) 6-(BOC-amino)-hexanoyl-Phe-Gly-AHCP-Ile AMPA, or a physiologically acceptable salt thereof;

b) 6-Amino-hexanoyl-Phe-Gly-AHCP-Ile ADPA, or a physiologically acceptable salt thereof;

c) 4-Dimethylamino-butyryl-Phe-Gly-AHCP-Ile AMPA, or a physiologically acceptable salt thereof;

d) 4-Aminopiperidinocarbonyl-Phe-Gly-AHCP-Ile AMPA, or a physiologically acceptable salt thereof;

e) 6-Methoxycarbonyl-hexanoyl-Phe-Gly-AHCP-Ile ADPA, or a physiologically acceptable salt thereof;

f) 6-Carboxy-hexanoyl-Phe-Gly-AHCP-Ile ADPA, or a physiologically acceptable salt thereof; or g) 4-Aminopiperidinocarbonyl-Phe-βAla-AHCP-Ile AMPA, or a physiologically acceptable salt thereof, each a compound of claim 1.

3. A compound according to claim 1, wherein $R^1$ is $R^6R^7N-$.

4. A compound according to claim 1, wherein $R^1$ is $R^6OOC-$.

5. A compound according to claim 1, wherein $R^1$ is $R^6-O-(CH_2CH_2O)_r-$.

6. A compound according to claim 1, wherein $R^1$ is $R^6R^7N-$, $R^7$ is H, A, tert.-butoxycarbonyl or benzyloxycarbonyl, $R^6R^7N$ can also be 4-aminopiperidino, Y is O, and p is 0, 1, 2, 3, 4, 5, 6 or 7.

7. A compound according to claim 1, wherein

R¹ is R⁶OOC—; and
Y is O.

8. A compound according to claim 1, wherein R⁶R⁷N is 4-aminopiperidino and y and p are each 0.

9. A compound according to claim 1, wherein —NH—CHR³—CR⁴—(CHR⁵)$_n$—CO— is AHCP.

10. A compound according to claim 1, wherein E is Ile or Leu.

11. A compound according to claim 1, wherein
Q is NH and
Y is A, 4-amino-2-methyl-5-pyrimidinylmethyl or 2-amino-5,6-dimethyl-3-pyrazinylmethyl.

12. A compound according to claim 1, wherein —Z—$C_mH_{2m}$—CO— is βAla.

13. A compound according to claim 1, wherein said compound is 4-amino-piperidinylcarbonyl-Phe-βAla-AHCP-Ile-AMPA or a physiologically acceptable salt thereof.

14. A pharmaceutical composition comprising a compound of claim 1 and a pharmaceutically acceptable carrier.

15. A pharmaceutical composition comprising about 10 mg-1 g of a compound of claim 1 and a pharmaceutically acceptable carrier.

16. A method of treating renin-dependent hypertension or hyperaldosteronism comprising administering an effective amount of a compound of claim 1.

17. A method according to claim 16, comprising administering doses of said compound in an amount of about 1–300 mg/kg of body weight.

18. A method of renin-dependent treating or prophylaxis of hypertension, renin-dependent cardiac insufficiency or renin-dependent hyperaldosteronism comprising administering an effective amount of a compound of claim 1.

19. A method according to claim 18, comprising administering daily doses of said compound in an amount of about 0.2–20 mg/kg of body weight.

20. A method of diagnosing renin as a factor in hypertension comprising administering to a subject suffering from hypertension 0.1–10 mg/kg of body weight of a compound according to claim 1.

21. A compound according to claim 1, wherein
R¹—$C_pH_{2p}$—(NH)$_y$ is BOC—NH—$C_pH_{2p}$—, $(CH_3)_2N$—$C_pH_{2p}$—, 4-piperidinylmethyl, 2-piperidino-ethyl, 3-pyrrolidino-propyl, 3-piperidino-propyl, 4-pyrrolidino-butyl, 4-piperidino-butyl, 4-BOC-amino-piperidino, $CH_3O$—$(CH_2)_2$—O—$(CH_2)_2$—O—$CH_2$—, 4-dimethylamino-piperidino, 4-ethoxycarbonyl-piperidino, 4-hydroxy-piperidino, 4-acetamido-piperidino, 4-amino-piperidino, 4-BOC-piperazino, 2-(2piperidinyl)-ethyl, 3-(2-piperidinyl)-propyl, 4-amino-piperidino-methyl, 4-guanidino-piperidino, 4-ureido-piperidino, 4-(N'-ethyl-ureido)-piperidino, 4-(N'-isopropyl-ureido)-piperidino, 4-methylamino-piperidino, 4-methyl-piperazino, CBZ—NH—$C_pH_{2p}$—, $CH_3O$—$(CH_2)_2$—O—$CH_2$—, $CH_3OOC$—$C_pH_{2p}$—, $(CH_3)_2N$—$(C_pH_{2p})$—NH—, $H_2N$—$C_pH_{2p}$— or piperazino;
—NH—CHR³—CR⁴—(CHR⁵)$_n$—CO— is AHCP, —NH—CH(isobutyl)—CHOH—$CH_2$—CH(isopropyl)—CO—, Sta, AHCH, AHPP, 2S—NH—CH($CH_2$-phenyl)—CHOH—$CH_2$—CH(isopropyl)—CO— or —NH—CH($CH_2$-cyclohexyl)—CHOH—$CH_2$—CH(isopropyl)—CO—;
E is Ile, Leu, Ala, Ile-Val or is absent; and
Q—Y is AMPA, —NH—$CH_2$–3-pyridyl, ADPA, —NH——$C_6H_4$—$SO_2NH_2$, OH, —NH—$(CH_2)_4$—OH, —NH—$(CH_2)_5$—OH, —NH—$(CH_2)_5$—$N(CH_3)_2$, —NH—$C_6H_{13}$, —NH—$CH_3$, —NH—(1-benzyl-4-piperidinyl), or —NH—CH(sec.-butyl)-(5-tetrazoyl).

* * * * *